US011426065B2

(12) United States Patent
Limon et al.

(10) Patent No.: US 11,426,065 B2
(45) Date of Patent: *Aug. 30, 2022

(54) APPARATUS, SYSTEM AND METHOD OF DETERMINING ONE OR MORE PARAMETERS OF A REFRACTIVE ERROR OF A TESTED EYE

(71) Applicant: 6 OVER 6 VISION LTD., Kfar Saba (IL)

(72) Inventors: Ofer Limon, Kfar Saba (IL); Alexander Zlotnik, Petah-Tikva (IL); Yair Kittenplon, Raanana (IL); Orna Bregman Amitai, Tel Aviv (IL)

(73) Assignee: 6 OVER 6 VISION LTD., Kfar Saba (IL)

( * ) Notice: Subject to any disclaimer, the term of this patent is extended or adjusted under 35 U.S.C. 154(b) by 219 days.

This patent is subject to a terminal disclaimer.

(21) Appl. No.: 16/750,307

(22) Filed: Jan. 23, 2020

(65) Prior Publication Data
US 2020/0237210 A1 Jul. 30, 2020

Related U.S. Application Data

(60) Provisional application No. 62/796,240, filed on Jan. 24, 2019.

(51) Int. Cl.
*A61B 3/028* (2006.01)
*G06T 7/55* (2017.01)
(Continued)

(52) U.S. Cl.
CPC ............ *A61B 3/028* (2013.01); *A61B 3/0025* (2013.01); *A61B 3/036* (2013.01); *A61B 3/09* (2013.01);
(Continued)

(58) Field of Classification Search
CPC ....... A61B 3/028; A61B 3/0025; A61B 3/036; A61B 3/09; A61B 3/103; G06T 7/0012;
(Continued)

(56) References Cited

U.S. PATENT DOCUMENTS

2011/0015541 A1*  1/2011  Padrick ..................... A61F 2/16
                                                        600/558
2013/0027668 A1*  1/2013  Pamplona .............. A61B 3/032
                                                        351/239
(Continued)

FOREIGN PATENT DOCUMENTS

EP        0956810 A1     11/1999
WO     2014195951 A1    12/2014

OTHER PUBLICATIONS

International Search Report and Written Opinion for International Patent Application No. PCT/IB2020/050536 dated May 21, 2020, 11 pages.

*Primary Examiner* — Mohammed A Hasan
(74) *Attorney, Agent, or Firm* — Dorsey & Whitney LLP

(57) ABSTRACT

Some demonstrative embodiments include apparatuses, systems and/or methods of determining one or more parameters of a refractive error of a tested eye. For example, a computing device may be configured to process depth mapping information to identify depth information of a tested eye; and to determine one or more parameters of a refractive error of the tested eye based on the depth information of the tested eye.

38 Claims, 11 Drawing Sheets

(51) Int. Cl.
    *G06T 7/521*     (2017.01)
    *G06T 7/00*     (2017.01)
    *A61B 3/036*     (2006.01)
    *A61B 3/09*     (2006.01)
    *A61B 3/00*     (2006.01)
    *G01S 17/08*     (2006.01)

(52) U.S. Cl.
    CPC ............ G06T 7/0012 (2013.01); G06T 7/521 (2017.01); G06T 7/55 (2017.01); *G01S 17/08* (2013.01); *G06T 2207/10028* (2013.01); *G06T 2207/30041* (2013.01)

(58) Field of Classification Search
    CPC . G06T 7/521; G06T 7/55; G06T 2207/10028; G06T 2207/30041; G01S 17/08; G01S 17/88; G01S 17/89
    USPC .......................................................... 351/208
    See application file for complete search history.

(56) References Cited

U.S. PATENT DOCUMENTS

| | | | |
|---|---|---|---|
| 2013/0100410 A1* | 4/2013 | Liang | A61B 3/1015 351/223 |
| 2016/0120402 A1* | 5/2016 | Limon | A61B 3/0025 351/241 |
| 2016/0135678 A1* | 5/2016 | Hernandez Castanedas | A61B 3/0025 351/206 |
| 2017/0215724 A1 | 8/2017 | Skolianos et al. | |
| 2018/0116500 A1* | 5/2018 | Escalier | A61B 3/036 |
| 2020/0225508 A1* | 7/2020 | Kittenpion | G01M 11/0221 |

\* cited by examiner

APPARATUS, SYSTEM AND METHOD OF DETERMINING ONE OR MORE PARAMETERS OF A REFRACTIVE ERROR OF A TESTED EYE

CROSS-REFERENCE

This application claims the benefit of and priority from U.S. Provisional Patent application No. 62/796,240, entitled "APPARATUS, SYSTEM AND METHOD OF DETERMINING ONE OR MORE PARAMETERS OF A REFRACTIVE ERROR OF A TESTED EYE", filed Jan. 24, 2019, the entire disclosure of which is incorporated herein by reference.

TECHNICAL FIELD

Embodiments described herein generally relate to determining one or more parameters of a refractive error of a tested eye.

BACKGROUND

A Refractive error (also referred to as a "refraction error") is a problem of an eye of focusing light accurately onto the retina, for example, due to the shape of the eye.

The most common types of refractive error are near-sightedness, far-sightedness, and astigmatism.

Refractive errors may be corrected with eyeglasses, contact lens, or surgery.

An eye examination for a patient may be performed by an eyewear prescriber, such as an optometrist or ophthalmologist, to determine one or more parameters for eyeglasses and/or contact lenses to construct and/or to dispense corrective lenses appropriate for the patient.

BRIEF DESCRIPTION OF THE DRAWINGS

For simplicity and clarity of illustration, elements shown in the figures have not necessarily been drawn to scale. For example, the dimensions of some of the elements may be exaggerated relative to other elements for clarity of presentation. Furthermore, reference numerals may be repeated among the figures to indicate corresponding or analogous elements. The figures are listed below.

DETAILED DESCRIPTION

Figure 1:
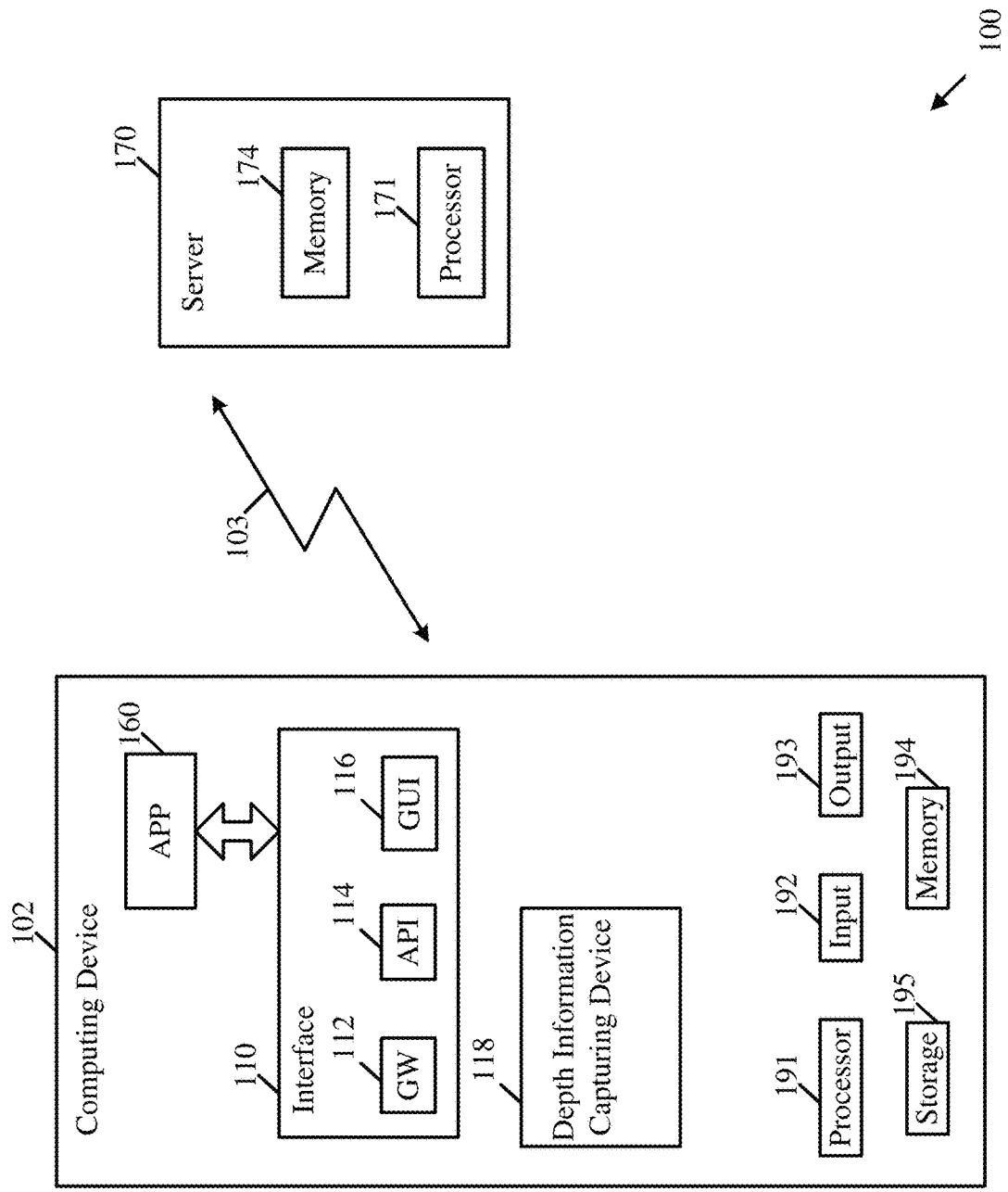
FIG. 1 is a schematic block diagram illustration of a system, in accordance with some demonstrative embodiments.

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, components, units and/or circuits have not been described in detail so as not to obscure the discussion.

Some portions of the following detailed description are presented in terms of algorithms and symbolic representations of operations on data bits or binary digital signals within a computer memory. These algorithmic descriptions and representations may be the techniques used by those skilled in the data processing arts to convey the substance of their work to others skilled in the art.

An algorithm is here, and generally, considered to be a self-consistent sequence of acts or operations leading to a desired result. These include physical manipulations of physical quantities. Usually, though not necessarily, these quantities capture the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

Discussions herein utilizing terms such as, for example, "processing", "computing", "calculating", "determining", "establishing", "analyzing", "checking", or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes.

The terms "plurality" and "a plurality", as used herein, include, for example, "multiple" or "two or more". For example, "a plurality of items" includes two or more items.

References to "one embodiment", "an embodiment", "demonstrative embodiment", "various embodiments" etc., indicate that the embodiment(s) so described may include a particular feature, structure, or characteristic, but not every embodiment necessarily includes the particular feature, structure, or characteristic. Further, repeated use of the phrase "in one embodiment" does not necessarily refer to the same embodiment, although it may.

As used herein, unless otherwise specified the use of the ordinal adjectives "first", "second", "third" etc., to describe a common object, merely indicate that different instances of like objects are being referred to, and are not intended to imply that the objects so described must be in a given sequence, either temporally, spatially, in ranking, or in any other manner.

Some embodiments, for example, may capture the form of an entirely hardware embodiment, an entirely software embodiment, or an embodiment including both hardware and software elements. Some embodiments may be implemented in software, which includes but is not limited to firmware, resident software, microcode, or the like.

Furthermore, some embodiments may capture the form of a computer program product accessible from a computer-usable or computer-readable medium providing program code for use by or in connection with a computer or any instruction execution system. For example, a computer-usable or computer-readable medium may be or may include any apparatus that can contain, store, communicate, propagate, or transport the program for use by or in connection with the instruction execution system, apparatus, or device.

In some demonstrative embodiments, the medium may be an electronic, magnetic, optical, electromagnetic, infrared, or semiconductor system (or apparatus or device) or a propagation medium. Some demonstrative examples of a computer-readable medium may include a semiconductor or solid state memory, magnetic tape, a removable computer diskette, a random access memory (RAM), a read-only memory (ROM), a FLASH memory, a rigid magnetic disk, and an optical disk. Some demonstrative examples of optical disks include compact disk-read only memory (CD-ROM), compact disk-read/write (CD-R/W), and DVD.

In some demonstrative embodiments, a data processing system suitable for storing and/or executing program code may include at least one processor coupled directly or indirectly to memory elements, for example, through a system bus. The memory elements may include, for example, local memory employed during actual execution of the program code, bulk storage, and cache memories which may provide temporary storage of at least some program code in order to reduce the number of times code must be retrieved from bulk storage during execution.

In some demonstrative embodiments, input/output or I/O devices (including but not limited to keyboards, displays, pointing devices, etc.) may be coupled to the system either directly or through intervening I/O controllers. In some demonstrative embodiments, network adapters may be coupled to the system to enable the data processing system to become coupled to other data processing systems or remote printers or storage devices, for example, through intervening private or public networks. In some demonstrative embodiments, modems, cable modems and Ethernet cards are demonstrative examples of types of network adapters. Other suitable components may be used.

Some embodiments may include one or more wired or wireless links, may utilize one or more components of wireless communication, may utilize one or more methods or protocols of wireless communication, or the like. Some embodiments may utilize wired communication and/or wireless communication.

Some embodiments may be used in conjunction with various devices and systems, for example, a mobile phone, a Smartphone, a mobile computer, a laptop computer, a notebook computer, a tablet computer, a handheld computer, a handheld device, a Personal Digital Assistant (PDA) device, a handheld PDA device, a mobile or portable device, a non-mobile or non-portable device, a cellular telephone, a wireless telephone, a device having one or more internal antennas and/or external antennas, a wireless handheld device, or the like.

Reference is now made to FIG. 1, which schematically illustrates a block diagram of a system 100, in accordance with some demonstrative embodiments.

As shown in FIG. 1, in some demonstrative embodiments system 100 may include a computing device 102.

In some demonstrative embodiments, device 102 may be implemented using suitable hardware components and/or software components, for example, processors, controllers, memory units, storage units, input units, output units, communication units, operating systems, applications, or the like.

In some demonstrative embodiments, device 102 may include, for example, a computing device, a mobile device, a mobile phone, a Smartphone, a Cellular phone, a notebook, a mobile computer, a laptop computer, a notebook computer, a tablet computer, a handheld computer, a handheld device, a PDA device, a handheld PDA device, a wireless communication device, or the like.

In some demonstrative embodiments, device 102 may include, for example, one or more of a processor 191, an input unit 192, an output unit 193, a memory unit 194, and/or a storage unit 195. Device 102 may optionally include other suitable hardware components and/or software components. In some demonstrative embodiments, some or all of the components of one or more of device 102 may be enclosed in a common housing or packaging, and may be interconnected or operably associated using one or more wired or wireless links. In other embodiments, components of one or more of device 102 may be distributed among multiple or separate devices.

In some demonstrative embodiments, processor 191 may include, for example, a Central Processing Unit (CPU), a Digital Signal Processor (DSP), one or more processor cores, a single-core processor, a dual-core processor, a multiple-core processor, a microprocessor, a host processor, a controller, a plurality of processors or controllers, a chip, a microchip, one or more circuits, circuitry, a logic unit, an Integrated Circuit (IC), an Application-Specific IC (ASIC), or any other suitable multi-purpose or specific processor or controller. Processor 191 may execute instructions, for example, of an Operating System (OS) of device 102 and/or of one or more suitable applications.

In some demonstrative embodiments, input unit 192 may include, for example, a keyboard, a keypad, a mouse, a touch-screen, a touch-pad, a track-ball, a stylus, a microphone, or other suitable pointing device or input device. Output unit 193 may include, for example, a monitor, a screen, a touch-screen, a flat panel display, a Light Emitting Diode (LED) display unit, a Liquid Crystal Display (LCD) display unit, a plasma display unit, one or more audio speakers or earphones, or other suitable output devices.

In some demonstrative embodiments, memory unit 194 includes, for example, a Random Access Memory (RAM), a Read Only Memory (ROM), a Dynamic RAM (DRAM), a Synchronous DRAM (SD-RAM), a flash memory, a volatile memory, a non-volatile memory, a cache memory, a buffer, a short term memory unit, a long term memory unit, or other suitable memory units. Storage unit 195 may include, for example, a hard disk drive, a Solid State Drive (SSD), or other suitable removable or non-removable storage units. Memory unit 194 and/or storage unit 195, for example, may store data processed by device 102.

In some demonstrative embodiments, device 102 may be configured to communicate with one or more other devices via a wireless and/or wired network 103.

In some demonstrative embodiments, network 103 may include a wired network, a local area network (LAN), a wireless LAN (WLAN) network, a radio network, a cellular network, a Wireless Fidelity (WiFi) network, an IR network, a Bluetooth (BT) network, and the like.

In some demonstrative embodiments, device 102 may allow one or more users to interact with one or more processes, applications and/or modules of device 102, e.g., as described herein.

In some demonstrative embodiments, device 102 may be configured to perform and/or to execute one or more operations, modules, processes, procedures and/or the like.

In some demonstrative embodiments, device 102 may be configured to determine one or more parameters of a refractive error (also referred to as a "refraction error") of a tested eye, for example, of a user and/or a patient, e.g., as described below.

In some demonstrative embodiments, the refractive error may include a problem of the tested eye, for example, in accurately focusing light onto a retina of the tested eye, for example, due to a shape of the tested eye.

In some demonstrative embodiments, the refractive error may include, for example, near-sightedness (also referred to as "myopia"), far-sightedness (also referred to as "hyperopia"), and/or astigmatism.

In one example, a refractive error of a tested eye may be corrected with an ophthalmic lens for the tested eye, or surgery.

For example, an ophthalmic lens may include a lens configured to improve vision.

In one example, the ophthalmic lens may be assembled, or configured to be assembled, in eyeglasses, e.g., of a patient, the user of device 102, and/or any other user.

In another example, the ophthalmic lens may include a contact lens, an intraocular lens, a swimming goggles lens, and the like.

In another example, the ophthalmic lens may include any other optical lens, e.g., a prescription lens or any other lens, configured to improve vision.

In some demonstrative embodiments, an eye examination may be performed by an eyewear prescriber, such as an optometrist or ophthalmologist, for example, to determine one or more optical parameters for the ophthalmic lens, for example, to construct and/or to dispense a corrective lens, e.g., appropriate for a patient.

In some demonstrative embodiments, the one or more optical parameters of the corrective lens may include a spherical power, a cylindrical power, a cylindrical axis of the corrective lens, and/or any other parameter of the corrective lens.

In some demonstrative embodiments, a degree of myopia or hyperopia may be correlated, for example, with a distance difference between a focal length of a lens of a tested eye and a retina of the tested eye, e.g., as described below.

Figure 2:
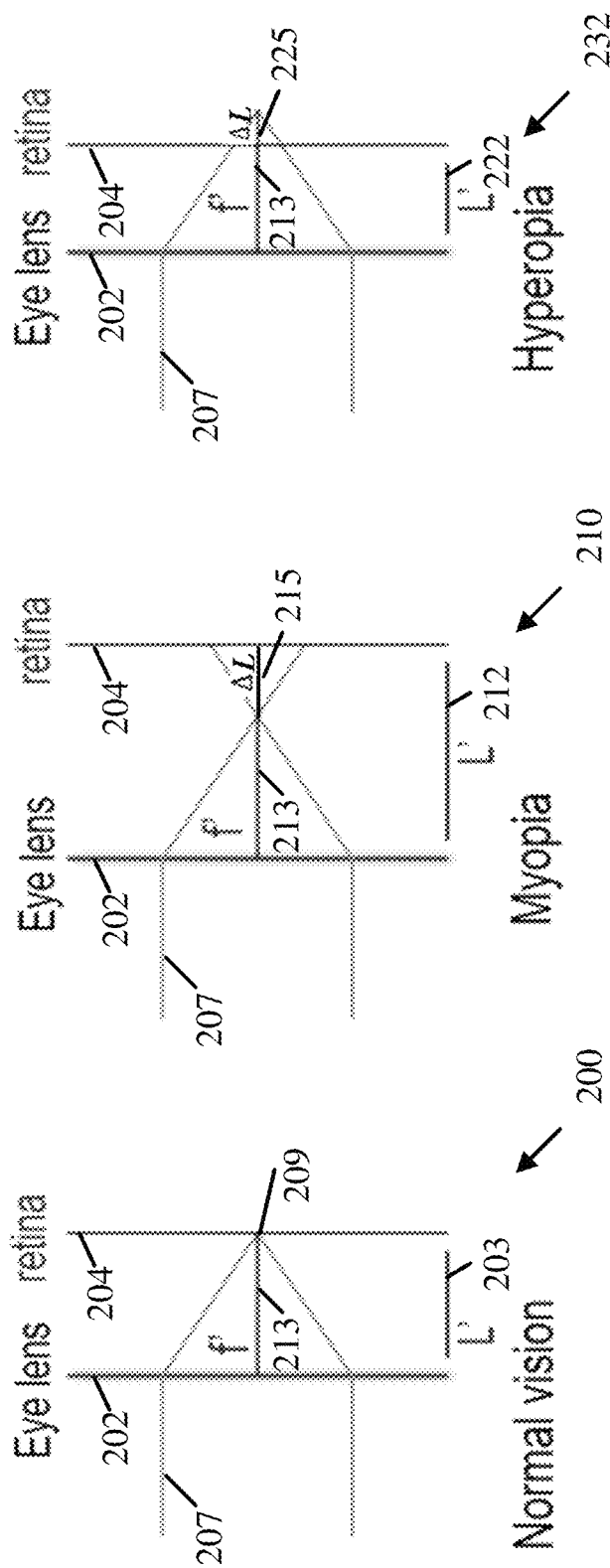
FIG. 2 is a schematic illustration of three eye models, which may be implemented in accordance with some demonstrative embodiments.

Reference is made to FIG. 2, which schematically illustrates three eye models, which may be implemented in accordance with some demonstrative embodiments.

In some demonstrative embodiments, the three eye models may use an eye model, e.g., a simplified eye model, including a lens 202 and a retina 204, e.g., which may replace some or all eye optics.

In some demonstrative embodiments, as shown in FIG. 2, light beams 207 directed on lens 202 may converge to a point 209, e.g., a spot, for example, which corresponds to a focal length of lens 202.

For example, light beams 207 may be provided by a light source, which is located in infinity, for example, on an optical axis of lens 202, e.g., perpendicular to a cornea of the tested eye.

In some demonstrative embodiments, point 209 may be at a focal distance 213, denoted f, from lens 202.

In some demonstrative embodiments, a first eye model 200 may illustrate a normal eye vision, e.g., as described below.

In some demonstrative embodiments, according to eye model 200, for example, a distance 203, denoted L', between lens 202 and retina 204 may be equal to focal distance 213. For example, a distance difference between focal distance 213 and distance 203 may be equal to zero.

In some demonstrative embodiments, a second eye model 210 may illustrate an eye having near-sightedness or myopia, e.g., as described below.

In some demonstrative embodiments, according to eye model 210, for example, a distance 212, between lens 202 and retina 204 may be longer than focal distance 213, which may result in near-sightedness or a myopia vision. For example, there may be a distance difference 215, denoted ΔL, between the focal distance 213 and distance 212.

In some demonstrative embodiments, a third eye model 220 may illustrate an eye having far-sightedness or a hyperopia, e.g., as described below.

In some demonstrative embodiments, according to eye model 220, for example, a distance 222, between lens 202 and retina 204 may be shorter than focal distance 213, which may result in far-sightedness or a hyperopia vision. For example, there may be a distance difference 225, denoted ΔL, between the focal distance 213 of lens 202 and distance 222.

Referring back to FIG. 1, in some demonstrative embodiments, system 100 may be configured to determine one or more parameters of a refractive error of a tested eye, for example, even without using any auxiliary optical means, e.g., as described below.

In one example, system 100 may be configured to determine the one or more parameters of the refractive error of the tested eye, for example, even without using a retinoscope, an automated refractor and/or any other auxiliary machine or elements.

In some demonstrative embodiments, the one or more parameters of the refractive error of the tested eye may include a correction factor to correct near-sightedness, far-sightedness, and/or a plurality of correction factors to correct an astigmatism, e.g., as described below.

In some demonstrative embodiments, system 100 may include at least one service, module, controller, and/or application 160 configured to determine the one or more parameters of the refractive error of the tested eye, e.g., as described below.

In some demonstrative embodiments, application 160 may include and/or may perform the functionality of an autorefractor or an automated refractor, e.g., configured to perform a refractive error analysis of the tested eye, e.g., as described below.

In some demonstrative embodiments, application 160 may include, or may be implemented as, software, a software module, an application, a program, a subroutine, instructions, an instruction set, computing code, words, values, symbols, and the like.

In some demonstrative embodiments, application 160 may include a local application to be executed by device 102. For example, memory unit 194 and/or storage unit 195 may store instructions resulting in application 160, and/or processor 191 may be configured to execute the instructions resulting in application 160 and/or to perform one or more calculations and/or processes of application 160, e.g., as described below.

In other embodiments, application 160 may include a remote application to be executed by any suitable computing system, e.g., a server 170.

In some demonstrative embodiments, server 170 may include at least a remote server, a web-based server, a cloud server, and/or any other server.

In some demonstrative embodiments, the server 170 may include a suitable memory and/or storage unit 174 having stored thereon instructions resulting in application 160, and a suitable processor 171 to execute the instructions, e.g., as descried below.

In some demonstrative embodiments, application 160 may include a combination of a remote application and a local application.

In one example, application 160 may be downloaded and/or received by the user of device 102 from another computing system, e.g., server 170, such that application 160 may be executed locally by users of device 102. For example, the instructions may be received and stored, e.g., temporarily, in a memory or any suitable short-term memory or buffer of device 102, e.g., prior to being executed by processor 191 of device 102.

In another example, application 160 may include a front-end to be executed locally by device 102, and a backend to be executed by server 170. For example, the front end may include and/or may be implemented as a local application, a web application, a web site, a web client, e.g., a Hypertext Markup Language (HTML) web application or the like.

For example, one or more first operations of determining the one or more parameters of the refractive error of the tested eye may be performed locally, for example, by device 102, and/or one or more second operations of determining the one or more parameters of the refractive error of the tested eye may be performed remotely, for example, by server 170, e.g., as described below.

In other embodiments, application 160 may include any other suitable computing arrangement and/or scheme.

In some demonstrative embodiments, system 100 may include an interface 110, e.g., a user interface, to interface between a user of device 102 and one or more elements of system 100, e.g., application 160.

In some demonstrative embodiments, interface 110 may be implemented using any suitable hardware components and/or software components, for example, processors, controllers, memory units, storage units, input units, output units, communication units, operating systems, and/or applications.

In some embodiments, interface 110 may be implemented as part of any suitable module, system, device, or component of system 100.

In other embodiments, interface 110 may be implemented as a separate element of system 100.

In some demonstrative embodiments, interface 110 may be implemented as part of device 102. For example, interface 110 may be associated with and/or included as part of device 102.

In one example, interface 110 may be implemented, for example, as middleware, and/or as part of any suitable application of device 102. For example, interface 110 may be implemented as part of application 160 and/or as part of an OS of device 102.

In some demonstrative embodiments, interface 110 may be implemented as part of server 170. For example, interface 110 may be associated with and/or included as part of server 170.

In one example, interface 110 may include, or may be part of a Web-based application, a web-site, a web-page, a plug-in, an ActiveX control, a rich content component, e.g., a Flash or Shockwave component, or the like.

In some demonstrative embodiments, interface 110 may be associated with and/or may include, for example, a gateway (GW) 112 and/or an Application Programming Interface (API) 114, for example, to communicate information and/or communications between elements of system 100 and/or to one or more other, e.g., internal or external, parties, users, applications and/or systems.

In some embodiments, interface 110 may include any suitable Graphic-User-Interface (GUI) 116 and/or any other suitable interface.

In some demonstrative embodiments, application 160 may be configured to determine the one or more parameters of the refractive error of the tested eye, for example, based on depth mapping information of the tested eye, e.g., as described below.

In some demonstrative embodiments, device 102 may include a depth information capturing device 118 or any other device or system, configured to capture, to create, and/or to determine the depth mapping information of an environment.

In one example, application 160 may be configured to determine the one or more parameters of the refractive error of the tested eye locally, for example, if application 160 is locally implemented by device 102. According to this example, depth information capturing device 118 may be configured to create the depth mapping information, and application 160 may be configured to receive the depth mapping information, e.g., from depth information capturing device 118, and to determine the one or more parameters of the refractive error of the tested eye, e.g., as described below.

In another example, application 160 may be configured to determine the one or more parameters of the refractive error of the tested eye remotely, for example, if application 160 is implemented by server 170, or if a back-end of application 160 is implemented by server 170, e.g., while a front-end of application 160 is implemented by device 102. According to this example, depth information capturing device 118 may be configured to create the depth mapping information; the front-end of application 160 may be configured to receive the depth mapping information; and server 170 and/or the back-end of application 160 may be configured to determine the one or more parameters of the refractive error of the tested eye, e.g., based on information received from the front-end of application 160.

In one example, device 102 and/or the front-end of application 160 may be configured to send the depth mapping information and, optionally, additional information, e.g., as described below, to server 170, e.g., via network 103; and/or server 170 and/or the back-end of application 160 may be configured to receive the depth mapping information, and to determine the one or more parameters of the refractive error of the tested eye, for example, based on the depth mapping information from device 102.

In some demonstrative embodiments, the depth mapping information may include at least one depth map, e.g., as described below.

In some demonstrative embodiments, the depth mapping information may include image information of one or more captured images, for example, Red Green Blue (RGB) image information and/or any other type of image information, e.g., as described below.

In another example, the depth mapping information may include any other additional or alternative information, which may be suitable for generating a depth map.

In some demonstrative embodiments, depth information capturing device 118 may include a depth mapper configured to provide a depth map of an environment, e.g., as described below.

In one example, the depth mapping information may include at least one depth map, for example, from the depth mapper.

In some demonstrative embodiments, the depth mapper may include an illuminator or a projector, and a depth sensor.

In some demonstrative embodiments, depth information capturing device 118 may include a structured-light system, for example, including a structured light projector to project a light structure, and a camera to capture the light structure.

In some demonstrative embodiments, depth information capturing device 118 may include a structured-light stereo camera, for example, including a structured light projector to project a light structure, and dual cameras.

In some demonstrative embodiments, depth information capturing device 118 may include an Infra Red (IR) source and an IR sensor, for example, in a structured-light system.

In some demonstrative embodiments, depth information capturing device 118 may include a Time of Flight (ToF) depth sensor, which may be configured to determine the depth mapping information according to a ToF measurement, e.g., as described below.

In other embodiments, depth information capturing device 118 may include any other device or system configured to create a depth map of an environment.

In some demonstrative embodiments, depth information capturing device 118 may include a multi camera device, e.g., as described below.

In one example, depth information capturing device 118 may provide the depth mapping information including image information, for example, from the multi-camera device.

In some demonstrative embodiments, depth information capturing device 118 may include a multi-camera device, for example, including two or more cameras, e.g., a dual camera, a stereo camera, multiple cameras or any other arrangement of multiple cameras.

In one example, depth information capturing device 118 may be configured to capture and generate a plurality of images from a plurality of respective cameras. For example, depth information capturing device 118 may capture a first image by a first camera and a second image by a second camera. According to this example, application 160 and/or depth information capturing device 118 may be configured to determine a depth map, for example, based on the first and second images, e.g., using image processing algorithms, methods, and/or the like.

In some demonstrative embodiments, depth information capturing device 118 may include a multi-axis depth mapper system, for example, including a plurality of depth mappers, e.g., as described below.

In some demonstrative embodiments, depth information capturing device 118 may include a multi-axis multi-camera system, for example, including a plurality of multi-camera devices, e.g., as described below.

In some demonstrative embodiments, depth information capturing device 118 may include any other additional or alternative sensors, elements, and/or components, which may be configured to create depth mapping information of an environment.

In one example, one or more calculations described herein may be suitable for implementations with a plurality of different types of depth information capturing device 118.

For example, one or more calculations may be configured and/or adjusted for the different types, for example, based on IR wavelength and/or visible light spectrum.

In some demonstrative embodiments, application 160 may be configured to determine the one or more parameters of the refractive error of the tested eye, for example, based on depth mapping information captured by depth information capturing device 118, for example, when depth information capturing device 118 is facing or aiming towards the tested eye, e.g., like capturing a "selfie", to capture the depth mapping information of the tested eye.

In one example, creation of the depth mapping information by depth information capturing device 118 may be based on a disparity of a point captured or projected from different coordinates, e.g., in the real world.

In some demonstrative embodiments, application 160 may be configured to use depth information and/or depth data of the tested eye, e.g., as captured by depth information capturing device 118, for example, to determine the one or more parameters of the refractive error of the tested eye, e.g., as described below.

In some demonstrative embodiments, application 160 may be configured to process depth mapping information captured by depth information capturing device 118, for example, to detect and/or identify depth information of the tested eye, e.g., as described below In some demonstrative embodiments, application 160 may be configured to process depth mapping information to identify depth information of a tested eye, e.g., as described below.

In some demonstrative embodiments, application 160 may be configured to determine one or more parameters of a refractive error of the tested eye, for example, based on the depth information of the tested eye, e.g., as described below.

In some demonstrative embodiments, the refractive error may include, for example, myopia, hyperopia, astigmatism including cylindrical power and/or cylindrical axis, and/or any other refractive error, e.g., as described below.

In some demonstrative embodiments, the one or more parameters of the refractive error of the tested eye may include, for example, a power correction factor to correct a lens power of the lens of the tested eye, e.g., as described below.

In some demonstrative embodiments, the depth mapping information may include at least one depth map from a depth mapper, for example, a depth mapper implemented by depth information capturing device 118, e.g., as described below.

In some demonstrative embodiments, application 160 may be configured to determine the one or more parameters of the refractive error of the tested eye, for example, by processing the depth information as depth information of a structured-light depth measurement, for example, from a structured-light depth sensor implemented by depth information capturing device 118, e.g., as described below.

In some demonstrative embodiments, application 160 may be configured to determine the one or more parameters of the refractive error of the tested eye by processing the depth information as depth information of a ToF measurement, for example, from a ToF depth sensor implemented by depth information capturing device 118, e.g., as described below.

In some demonstrative embodiments, the depth mapping information may include image information from a multi-camera device, for example, when depth information capturing device 118 includes the multi-camera device, e.g., as described below.

In some demonstrative embodiments, application 160 may be configured to determine the one or more parameters of the refractive error of the tested eye, for example, by processing the depth information as depth information of a multi-camera depth measurement, for example, from a multi-camera device implemented by depth information capturing device 118, e.g., as described below.

In some demonstrative embodiments, application 160 may be configured to determine the one or more parameters of the refractive error of the tested eye, for example, based on a depth value of the tested eye, e.g., as described below.

In some demonstrative embodiments, application 160 may be configured to identify, for example, based on the depth mapping information, a depth value captured via a lens of the tested eye, and to determine the one or more parameters of the refractive error of the tested eye, for example, based on the depth value, e.g., as described below.

In some demonstrative embodiments, the depth value captured via the lens of the tested eye may include, for example, a depth value corresponding to a retina of the tested eye, e.g., as described below.

In some demonstrative embodiments, application 160 may be configured to determine the one or more parameters of the refractive error of the tested eye, for example, based on a distance between the tested eye and the depth information capturing device 118, e.g., as described below.

In some demonstrative embodiments, application 160 may be configured to determine the distance between the tested eye and the depth information capturing device 118, for example, based on the depth mapping information, e.g., as described below.

In some demonstrative embodiments, application 160 may be configured to identify, for example, based on the depth mapping information, a depth value corresponding to a predefined area of the tested eye, and to determine the distance between the tested eye and the depth information capturing device 118, for example, based on the depth value corresponding to the predefined area, e.g., as described below.

In some demonstrative embodiments, the predefined area of the tested eye may include a sclera of the tested eye, an opaque area around a pupil of the tested eye, and/or any other area of the tested eye, e.g., as described below.

In some demonstrative embodiments, application 160 may be configured to determine the distance between the tested eye and the depth information capturing device 118, for example, based on position information corresponding to a position of the depth information capturing device 118, e.g., as described below.

In one example, the position information may be received, for example, from a positioning sensor of device 102, e.g., an accelerometer, an inertial measurement unit, and/or the like.

In some demonstrative embodiments, application 160 may be configured to determine the one or more parameters of the refractive error of the tested eye, for example, by determining a power correction factor, denoted ΔP, e.g., as follows:

$$\Delta P = -\text{sign}(u') * \frac{1}{(u' - d)} \quad (1)$$

wherein u' denotes a depth value, for example, based on the depth mapping information, and d denotes a distance value, for example, based on the distance between the tested eye and the depth information capturing device 118, e.g., as described below.

In one example, the depth value u' may include a depth value corresponding to the retina of the tested eye, which may be captured via the lens of the tested eye, e.g., as described below.

In some demonstrative embodiments, the distance between the tested eye and the depth information capturing device 118 may include, for example, a predefined distance, e.g., as described below.

In some demonstrative embodiments, application 160 may be configured to cause user interface 110 to instruct a user of device 102 to position the depth information capturing device 118 for capturing the depth mapping information, for example, at a predefined distance from the tested eye, e.g., as described below.

In one example, user interface 110 may instruct the user, for example, using guidance instructions that may appear on a screen of device 102, e.g., a display of a mobile phone.

In another example, user interface 110 may instruct the user, for example, using voice instructions.

In another example, user interface 110 may instruct the user using any other additional or alternative method.

In some demonstrative embodiments, application 160 may be configured to determine the one or more parameters of the refractive error of the tested eye, for example, based on first and second different depth values, e.g., as described below.

In some demonstrative embodiments, application 160 may be configured to identify a first depth value corresponding to a first area of the tested eye, for example, based on the depth mapping information, e.g., as described below.

In some demonstrative embodiments, application 160 may be configured to identify a second depth value corresponding to a second area of the tested eye, for example, based on the depth mapping information, e.g., as described below.

In some demonstrative embodiments, the first area may include a pupil of the tested eye, and/or the second area may include an area around the pupil of the tested eye, e.g., as described below.

In other embodiments, the first area and/or the second area may include any other areas.

In some demonstrative embodiments, application 160 may be configured to determine the one or more parameters of the refractive error of the tested eye, for example, based on the first and second depth values, e.g., as described below.

In some demonstrative embodiments, application 160 may be configured to determine the one or more parameters of the refractive error of the tested eye, for example, based on first and second pluralities of different depth values, e.g., as described below.

In some demonstrative embodiments, application 160 may be configured to identify a first plurality of depth values corresponding to the first area of the tested eye, for example, based on the depth mapping information, e.g., as described below.

In some demonstrative embodiments, application 160 may be configured to identify a second plurality of depth values corresponding to the second area of the tested eye, for example, based on the depth mapping information, e.g., as described below.

In some demonstrative embodiments, application 160 may be configured to determine the one or more parameters of the refractive error of the tested eye, for example, based on the first and second pluralities of depth values, e.g., as described below.

In some demonstrative embodiments, application 160 may be configured to determine a distance value, for example, based on the first plurality of depth values, e.g., as described below.

In one example, application 160 may determine the distance value d between the tested eye and the depth information capturing device 118, for example, based on the first plurality of depth values.

In some demonstrative embodiments, application 160 may be configured to determine a depth value, for example, based on the second plurality of depth values, e.g., as described below.

In one example, application 160 may determine the depth value u' corresponding to the retina of the tested eye, which may be captured via the lens of the tested eye, for example, based on the second plurality of depth values.

In some demonstrative embodiments, application 160 may be configured to determine the one or more parameters of the refractive error of the tested eye, for example, based on the depth value and the distance value, e.g., as described below.

In one example, application 160 may determine the one or more parameters of the refractive error of the tested eye, for example, based on the distance value d and the depth value u', e.g., according to Equation 1, e.g., as described above.

In some demonstrative embodiments, the depth mapping information may be captured via a mirror, for example, to increase the distance between the tested eye and the depth information capturing device 118, e.g., as described below In some demonstrative embodiments, application 160 may be configured to cause user interface 110 to instruct the user of device 102 to position the depth information capturing device 118 facing a mirror, for example, such that the depth mapping information may be captured by depth information capturing device 118 via the mirror, e.g., as described below.

In some demonstrative embodiments, the user of device 102 may use an ophthalmic lens for vision, e.g., a contact lens or a lens of eyeglasses, and accordingly, the depth information may include depth information captured via the ophthalmic lens, e.g., as described below.

In some demonstrative embodiments, application 160 may be configured to determine the one or more parameters of the refractive error of the tested eye by processing the depth information as depth information captured via an ophthalmic lens, e.g., as described below.

In some demonstrative embodiments, application 160 may be configured to determine the one or more parameters of the refractive error of the tested eye, for example, by processing the depth information as depth information captured via a lens of eyeglasses at a vertex distance from the tested eye, for example, when the user wears eyeglasses including the ophthalmic lens, e.g., as described below.

In some demonstrative embodiments, application 160 may be configured to determine the one or more parameters of the refractive error of the tested eye by processing the depth information as depth information captured via a contact lens on the tested eye, for example, when the user wears the contact lens, e.g., as described below.

In some demonstrative embodiments, application 160 may be configured determine the one or more parameters of the refractive error of the tested eye, for example, based on one or more parameters of the ophthalmic lens, e.g., as described below.

In some demonstrative embodiments, application 160 may be configured to determine the one or more parameters of the refractive error of the tested eye, for example, based on depth mapping information including a single depth map, e.g., as described below.

In some demonstrative embodiments, application 160 may be configured to determine the one or more parameters of the refractive error of the tested eye, for example, based on depth mapping information including a plurality of different depth mapping information inputs, e.g., as described below.

In some demonstrative embodiments, application 160 may be configured to process a plurality of different depth mapping information inputs, for example, corresponding to a different plurality of relative positions between depth information capturing device 118 and the tested eye, e.g., as descried below.

In some demonstrative embodiments, the plurality of different depth mapping information inputs may include at least a first depth mapping information input, and a second depth mapping information input, e.g., as described below.

In some demonstrative embodiments, the first depth mapping information input may be captured at a first relative position, for example, between the depth information capturing device 118 and the tested eye, e.g., as described below.

In some demonstrative embodiments, the second depth mapping information input may be captured at a second relative position, different from the first position, for example, between the depth information capturing device 118 and the tested eye, e.g., as described below.

In some demonstrative embodiments, application 160 may be configured to cause user interface 110 to instruct the user to change a relative positioning between depth information capturing device 118 and the tested eye, for example, for capturing the first depth mapping information input at the first relative position and the second depth mapping information input at the second relative position, e.g., as described below.

In some demonstrative embodiments, the first relative position may include, for example, a first relative distance between the depth information capturing device 118 and the tested eye, e.g., as described below.

In some demonstrative embodiments, the second relative position may include, for example, a second relative distance, different from the first relative distance, between the depth information capturing device 118 and the tested eye, e.g., as described below.

In some demonstrative embodiments, the first relative position may include a first relative angle between a depth capturing meridian and a vertical meridian of the tested eye, e.g., as described below.

In some demonstrative embodiments, the second relative position may include a second relative angle, different from the first relative angle, between the depth capturing meridian and the vertical meridian of tested eye, e.g., as described below.

In some demonstrative embodiments, application 160 may be configured to process the plurality of different depth mapping information inputs, for example, corresponding to a different plurality of depth capturing devices 118, e.g., as descried below.

In some demonstrative embodiments, application 160 may be configured to process the first and second depth mapping information inputs, for example, based on an angle between a first depth capturing meridian of a first depth information capturing device to capture the first depth mapping information input, and a second depth capturing meridian of a second depth information capturing device to capture the second depth mapping information input, e.g., as descried below.

In some demonstrative embodiments, application 160 may be configured to determine a cylindrical axis of the tested eye and/or a cylindrical power of the tested eye, for example, based on the plurality of different depth mapping information inputs, e.g., as descried below.

In some demonstrative embodiments, application 160 may be configured to reduce an accommodation error of the tested eye, for example, when the depth mapping information is captured, e.g., as descried below.

In some demonstrative embodiments, application 160 may be configured to cause a graphic display, e.g., of output 193, to display a predefined pattern configured to reduce an accommodation error of the tested eye, e.g., as descried below.

In some demonstrative embodiments, application 160 may be configured to instruct a user of device 102 to capture the depth mapping information, for example, including the depth information of a tested eye, e.g., as described below.

In some demonstrative embodiments, application 160 may be configured to instruct the user of device 102 to place and/or position device 102 such that depth information capturing device 118 is facing or is directed towards the tested eye, for example, to enable application 160 to detect and/or to identify the depth information of the tested eye, e.g., in the depth mapping information.

In some demonstrative embodiments, a camera of depth information capturing device 118 may be configured to capture an eye image, e.g., an RGB image and/or any other image, of the tested eye, for example, when the depth mapping information is captured by depth information capturing device 118, e.g., as described below.

In some demonstrative embodiments, application 160 may be configured to detect and/or identify the depth information of the tested eye, for example, based on a comparison and/or a correlation between the depth mapping information and eye image of the tested eye, e.g., as described below.

In some demonstrative embodiments, application 160 may be configured to determine one or more parameters of the refractive error of the tested eye, for example, based on the depth mapping information of the tested eye, and distance information corresponding to a distance between depth information capturing device 118 and the tested eye, for example, when the depth mapping information is captured by depth information capturing device 118, e.g., as described below.

In some demonstrative embodiments, the depth mapping information of the tested eye may be captured by depth information capturing device 118 via a lens of the tested eye, e.g., lens 202 (FIG. 2), e.g., as described below.

In some demonstrative embodiments, the depth mapping information of the tested eye captured by depth information capturing device 118 may be captured via an ophthalmic lens, e.g., as described below.

In some demonstrative embodiments, the depth information of the tested eye may correspond to a retina of the tested eye captured via the lens of the tested eye, e.g., as described below.

In some demonstrative embodiments, the distance between depth information capturing device 118 and the tested eye, for example, when the depth mapping information is captured, may include a predefined distance, e.g., as described below.

In some demonstrative embodiments, application 160 may be configured to instruct the user of device 102 to place and/or position device 102 such that depth information capturing device 118 is at the predefined distance from the tested eye, e.g., as described below.

In some demonstrative embodiments, the distance between depth information capturing device 118 and the tested eye, for example, when the depth mapping information is captured, may be determined and/or calculated, e.g., as descried below.

In some demonstrative embodiments, application 160 may be configured to determine the distance between depth information capturing device 118 and the tested eye, for example, based on the depth information, e.g., as described below.

In one example, application 160 may determine the distance between depth information capturing device 118 and the tested eye, for example, based on depth information of an area around a pupil of the tested eye, e.g., as described below.

In another example, application 160 may determine the distance between depth information capturing device 118 and the tested eye, for example, based on depth information of an opaque object of the tested eye, e.g., the sclera or any other object.

In another example, application 160 may determine the distance between depth information capturing device 118 and the tested eye, for example, based on an analysis of the depth mapping information of the tested eye, e.g., to identify the sclera or any other object of the tested eye, e.g., as described below.

In another example, application 160 may determine the distance between depth information capturing device 118 and the tested eye, for example, based on one or more sensors of device 102, for example, an accelerometer and/or any other sensor, e.g., as described below.

In another example, application 160 may determine the distance between depth information capturing device 118 and the tested eye based on any other additional or alternative algorithm and/or method.

In some demonstrative embodiments, application 160 may be configured to determine depth information, e.g., a depth value, corresponding to a retina of the tested eye, e.g., a reflex on the retina of the tested eye, for example, to determine the one or more parameters of the refractive error of the tested eye, e.g., as described below.

In another example, application 160 may determine the depth information of the reflex on the retina, for example, based on an analysis of the depth mapping information of the tested eye, e.g., as described below.

In some demonstrative embodiments, the one or more parameters of the refractive error of the tested eye may include a power correction factor to correct a lens power of the lens of the tested eye, e.g., in an eye meridian of the tested eye corresponding to a plane of depth information capturing device 118, e.g., as described below.

In some demonstrative embodiments, the power correction factor, e.g., when applied to a corrective lens, may shift an image of a point source to be on the retina, which may result in substantially normal eye vision, e.g., using the corrective lens. For example, the power correction factor, e.g., when applied to a correction lens, may shift point 209 (FIG. 2) of eye models 210 and/or 220 towards retina 204 (FIG. 2), e.g., as described above.

In some demonstrative embodiments, for example, when the refractive error includes myopia and/or hyperopia, applying the power correction factor to a corrective lens for the tested eye may allow achieving a normal eye vision with the corrective lens, e.g., since the lens power of the lens of the tested eye may be equal across all meridians of the tested eye, for example, when the refractive error includes myopia and/or hyperopia.

In some demonstrative embodiments, a plurality of power correction factors corresponding to a plurality of meridians of the tested eye may be applied to a corrective lens, for example, when the refractive error includes a cylinder error, e.g., as described below.

In one example, a power correction factor, denoted $\Delta P_{\theta i}$, e.g., an optimal power correction, may be configured to correct a lens power, denoted $P_{\theta i}$, at a certain meridian, denoted $\theta i$, of the tested eye, e.g., from a possible set of meridians, denoted $\{\theta i\} i$. For example, the meridian $\theta i$ may be measured relative to a vertical meridian of the tested eye. According to this example, if the power correction factor $\Delta P_{\theta i}$ is applied over a cornea of the tested eye or over a contact lens plane, a total corrected power of the tested eye may be determined as $\Delta P_\theta + P_{\theta i}$.

For example, the power correction factor $\Delta P_{\theta i}$ may satisfy a condition that a total focal length of the tested eye at a certain meridian $\theta i$, e.g., the total corrected power of the tested eye $\Delta P_\theta + P_{\theta i}$, may match exactly a length of an eyeball of the tested eye, for example, a length between the retina and the lens of the tested eye, e.g., lengths 212 and/or 222 (FIG. 2). For example, the power correction factor $\Delta P\theta i$ may adjust, e.g., bring back, the focal plane to the retina.

In some demonstrative embodiments, the effective focal length of the tested eye f' may be based on a combination of some or even all eye refractive surfaces and a geometrical structure of the tested eye, for example, a power of the cornea, a crystalens or Intraocular Lens (IOL) power, and the like.

In some demonstrative embodiments, application 160 may be configured to determine the power correction factor $\Delta P_{\theta i}$, e.g., even at any given meridian, to a given focal length of the tested eye, which may provide an increased, e.g., an optimal, visual acuity.

In some demonstrative embodiments, application 160 may determine the power correction factor, e.g., even at any given meridian, for example, based on a reflected light from the retina of the tested eye, e.g., as described below.

In some demonstrative embodiments, application 160 may be configured to determine the optical power correction factor $\Delta P_{\theta i}$ to the effective focal length $P_\theta$ of the tested eye, for example, to match the length of an eyeball of the tested eye, for example, by using an analysis of a reflected light from a retina of the tested eye, for example, in a way which may provide an optimal visual acuity, e.g., as described below.

Figure 3A:
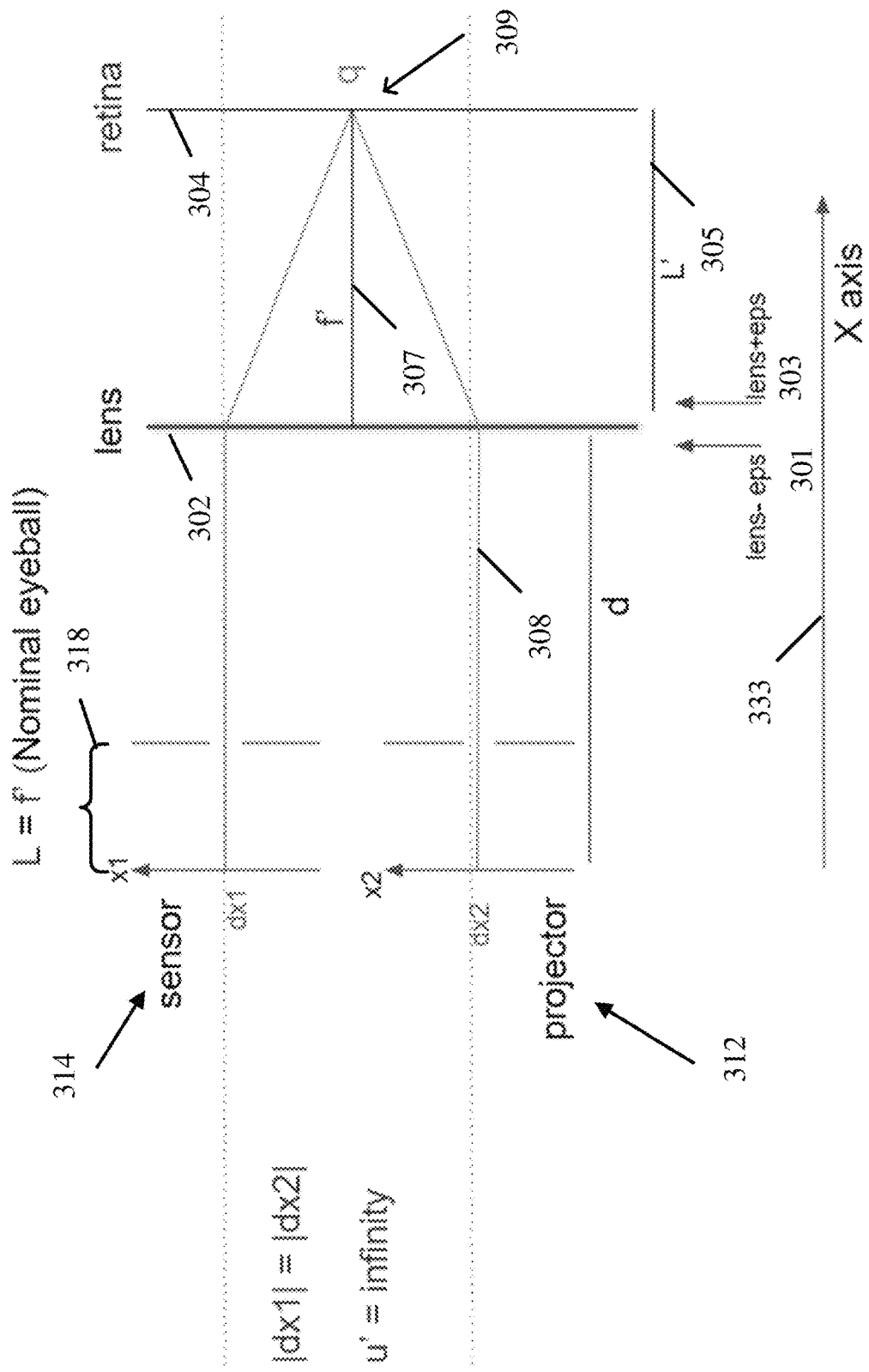
FIGS. 3A, 3B and 3C are schematic illustrations of three respective measurement schemes, in accordance with some demonstrative embodiments.
Figure 3B:
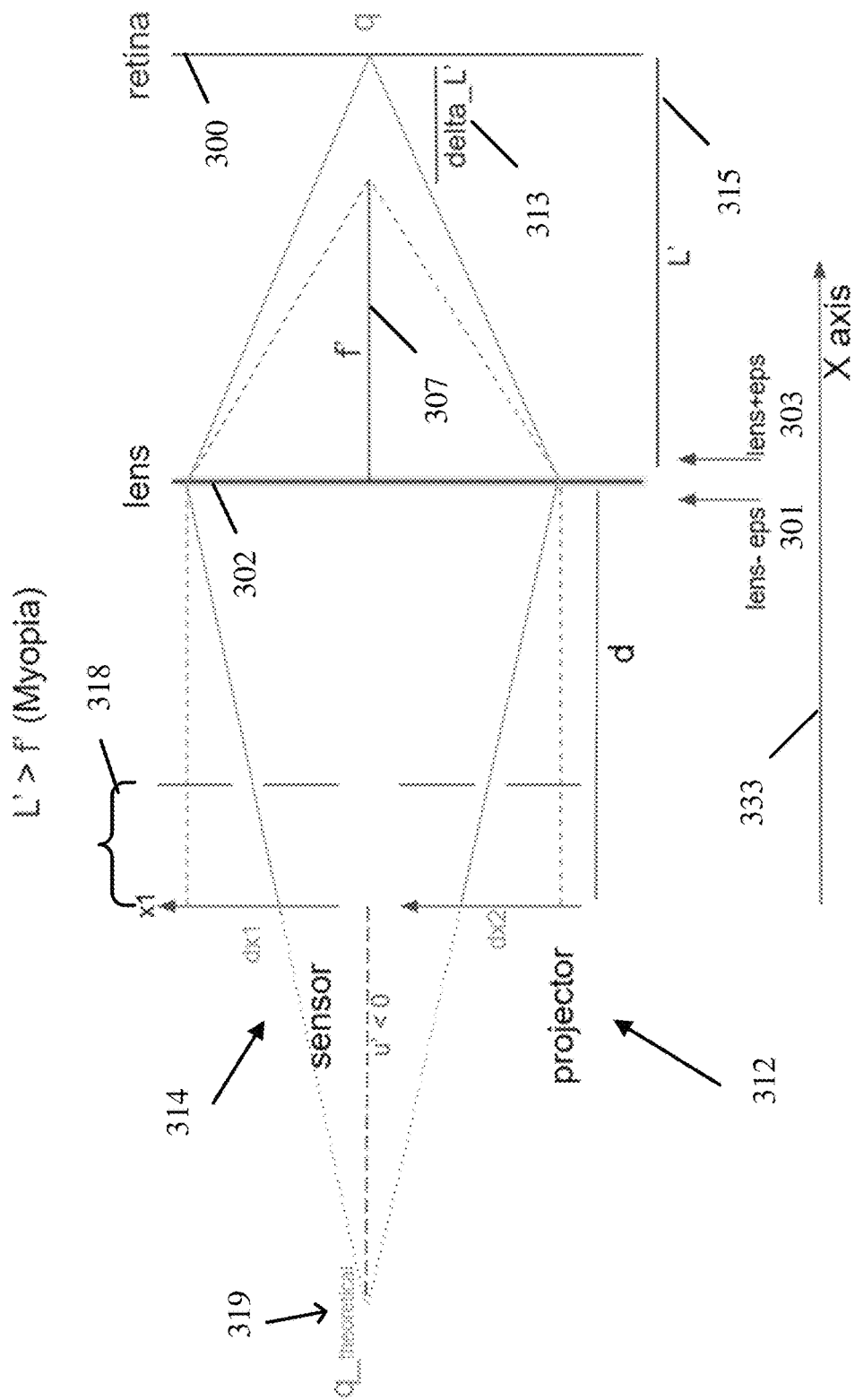
Figure 3C:
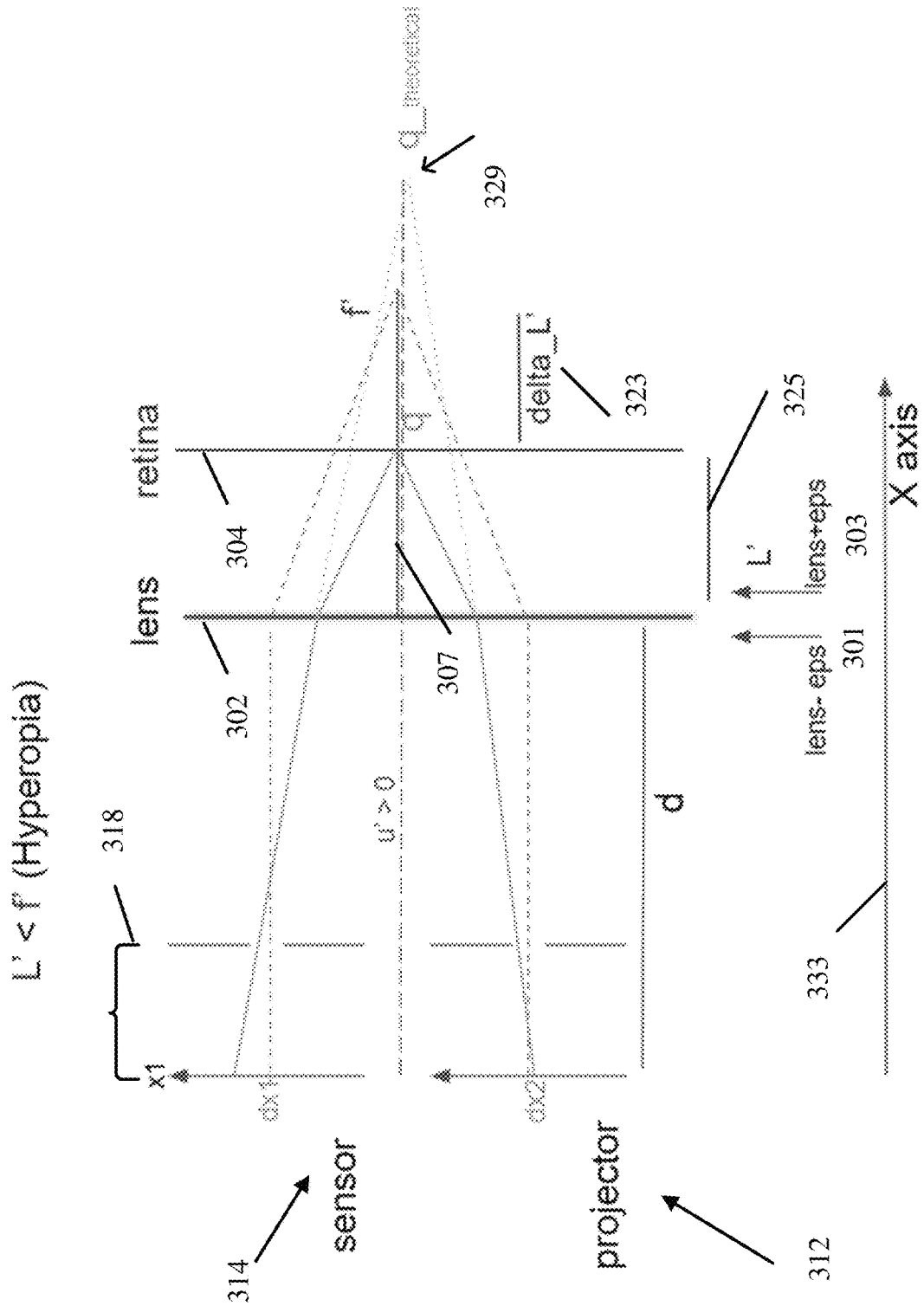

Reference is made to FIGS. 3A, 3B and 3C, which schematically illustrate three respective measurement schemes, in accordance with some demonstrative embodiments.

In some demonstrative embodiments, the measurement schemes of FIGS. 3A, 3B and 3C may be used to measure power correction factors for three different eye visions, e.g., as described below.

In some demonstrative embodiments, as shown in FIGS. 3A, 3B and 3C, the measurement schemes may include a depth mapper 318 including a projector or an illuminator 312, and a depth sensor 314. For example, depth information capturing device 118 (FIG. 1) may be configured to perform one or more operations of, the functionality of, and/or the role of depth mapper 318.

In some demonstrative embodiments, as shown in FIGS. 3A, 3B and 3C, projector 312 may be configured to project a light beam 308 towards a lens 302 of a tested eye, and depth sensor 314 may be configured to sense a reflection of a feature, denoted q, modeled as a point, which may correspond to a reflection of light beam 308 on a retina 304 of the tested eye.

In one example, the feature q may include a reflex on retina 304 of the light beam 308, or any other reflex and/or feature.

In some demonstrative embodiments, depth sensor 314 may be configured to determine a sensed depth, denoted u', of the feature q, for example, when the feature q is sensed via lens 302, e.g., as described below.

In some demonstrative embodiments, the measurement scheme of FIG. 3A may correspond to a normal eye vision of a tested eye.

In some demonstrative embodiments, as shown in FIG. 3A, a focal length 307, denoted f', e.g., an effective focal length, of lens 302 of the tested eye, may be equal to a distance 305, between lens 302 and retina 304 of the tested eye.

According to these embodiments, the reflection of the feature q may be sensed by depth sensor 314 of depth mapper 318 to appear at a location 309.

In some demonstrative embodiments, as shown in FIG. 3A, location 309 may be sensed by depth mapper 318 to appear on retina 304, for example, for a normal eye vision.

In some demonstrative embodiments, as shown in FIG. 3B, the focal length 307 may be shorter than a length 315, denoted L', between lens 302 and retina 304, which may result in near-sightedness vision, e.g., myopia.

In some demonstrative embodiments, application 160 (FIG. 1) may be configured to determine a correction factor 313, denoted delta_L', for the near-sightedness vision, e.g., as described below.

In some demonstrative embodiments, correction factor 313 may be configured to match the focal length 307 to the length 315 between lens 302 and retina 304, e.g., as described below.

In some demonstrative embodiments, as shown in FIG. 3C, the focal length 307 may be longer than a length 325, denoted L', between lens 302 and retina 304, which may result in far-sightedness vision, for example, hyperopia.

In some demonstrative embodiments, application 160 (FIG. 1) may be configured to determine a correction factor 323, denoted delta_L', for the far-sightedness vision e.g., as described below.

In some demonstrative embodiments, correction factor 323 may be configured to match the focal length 307 to the length 325 between lens 302 and retina 304, e.g., as described below.

In some demonstrative embodiments, application 160 (FIG. 1) may be configured to determine a correction factor, e.g., correction factors 313 and/or 323, based on a distance, denoted d, between depth mapper 318 and lens 302, for example, when depth information is captured by depth mapper 318, e.g., as described below.

In some demonstrative embodiments, application 160 (FIG. 1) may be configured to determine the correction factor, e.g., correction factors 313 and/or 323, based on the sensed depth u', which may be sensed by depth mapper 318, e.g., as described below.

In some demonstrative embodiments, the correction factor, e.g., correction factors 313 and/or 323, may be based on a vergence, denoted "Verge'$_x$," of the feature q at a point x on an X-axis 333, e.g., an optical axis of depth mapper 318.

In some demonstrative embodiments, a vergence value may describe a curvature of an optical wave front. For example, the vergence value may be positive for convergence and/or negative for divergence. The vergence value may be determined based on a refractive index of a medium, denoted n, and a distance, denoted r, from a point source to a wave front. For example, the vergence value may be defined as an n/r. In one example, it may be assumed that the refractive index of the medium n, may be equal to one, e.g., n=1, for example, for simplicity of calculations. In another example, other values of the refractive index n may be used.

In some demonstrative embodiments, sensor 314 of depth mapper 318 may be configured to determine the sensed depth u', corresponding to the feature q captured via lens 302, e.g., as described below.

In some demonstrative embodiments, the correction factor, e.g., correction factors 313 and/or 323, may be based on a first vergence of the feature q at a first point on the X-axis 333, and a second vergence of the feature q at a second point on the X-axis 333.

In some demonstrative embodiments, the first vergence may include a vergence, denoted $$Verge'_{lens_{\varepsilon_+}},$$

of the feature q at a point 303 ($lens_{\varepsilon_+}$) on X-axis 331, which is at close proximity to a first side of lens 302, e.g., at a distance epsilon from the right side of the lens 302.

In some demonstrative embodiments, the second vergence may include a vergence, denoted $$Verge'_{lens_{\varepsilon_-}},$$

of the feature q at a point 301 ($lens_{\varepsilon_-}$) on X-axis 331, which is at close proximity to a second side of lens 302, e.g., at a distance epsilon from the left side of the lens 302.

In some demonstrative embodiments, a sensor vergence, denoted $Verge'_{sensor}$, of the feature q at a location of the sensor 314 may be based on the sensed depth u', which may be at a theoretical location, denoted $q_{\_theorethical}$, e.g., as follows:

$$Verge'_{sensor} = \text{sign}(u') * \left|\frac{1}{u'}\right| \qquad (2)$$

In one example, as shown in FIG. 3B, the sensed depth u' may correspond to the theoretical location $q_{\_theorethical}$, which is at a location 319.

In one example, as shown in FIG. 3C, the sensed depth u' may correspond to the theoretical location $q_{\_theorethical}$, which is at a location 329.

Accordingly, the second vergence, e.g., at the point 301, may be determined, e.g., as follows:

$$Verge'_{lens_{\varepsilon_-}} = \text{sign}(u') * \frac{1}{(u'-d)} \qquad (3)$$

An actual vergence of the feature q at the points 301 and 303, may be determined, e.g., as follows:

$$Verge'_{lens_{\varepsilon_+}} = \frac{-1}{L'} \qquad (4)$$

$$Verge'_{lens_{\varepsilon_-}} = \frac{-1}{L'} + P_{eyelens} = \frac{-1}{L'} + \frac{1}{f'} \qquad (5)$$

For example, Equation 4 and Equation 5 may be combined, for example, to form a thin lens equation, e.g., as follows:

$$\text{sign}(u') * \frac{1}{(u'-d)} = \frac{-1}{L'} + \frac{1}{f'} \qquad (6)$$

In some demonstrative embodiments, the power correction $\Delta P_{\theta_i}$, e.g., power correction factors 313 and/or 323, may be configured to match the focal length 307 of the tested eye to the physical length of an eyeball L' of the tested eye, for example, to match the focal length 307 to length 315 and/or to length 325, respectively, e.g., as follows:

$$L' = \frac{1}{P_{eyelens} + \Delta P_{\theta_i}} = \frac{1}{\frac{1}{f'} + \Delta P_{\theta_i}} \qquad (7)$$

For example, the power correction M may be determined by substituting Equation 7 into Equation 6, e.g., as follows:

$$\text{sign}(u') * \frac{1}{(u'-d)} = \frac{-1}{f'} - \Delta P_{\theta_i} + \frac{1}{f'} = -\Delta P_{\theta_i} \qquad (8)$$

$$\Delta P_{\theta_i} = -\text{sign}(u') * \frac{1}{(u'-d)} \qquad (9)$$

In some demonstrative embodiments, as per Equation 9, the power correction factor $\Delta P_{\theta_i}$ of the tested eye may be determined, for example, based on the distance d between depth mapper 318 and lens 302, and the sensed depth u' of the feature q, e.g., sensed by depth mapper 318.

In some demonstrative embodiments, depth mapper 318 may be configured to capture depth mapping information of the tested eye; application 160 (FIG. 1) may be configured to detect the sensed depth u' of the feature q in the depth map; application 160 (FIG. 1) may be configured to determine the distance d, for example, based on the depth mapping information and/or based on any other distance information; and/or application 160 (FIG. 1) may be configured to determine the power correction factor $\Delta P_{\theta_i}$ of the tested eye, for example, using the distance d and the sensed depth u', e.g., according to Equation 9.

In some demonstrative embodiments, one or more test cases may be used, for example, to validate Equation 9, e.g., as described below.

In one example, a first test case, e.g., an extreme test case, in which an eyeball of the tested eye is nominal, e.g., a normal vision, may be applied to Equation 9. According to this example, the length between lens 302 and retina 304 may be equal to the focal length 307, for example, L'=f', e.g., as shown in FIG. 3A, and, accordingly, Equation 9 may result in a value of zero, which means that no power correction factor is required, e.g., as follows:

$$u' = \infty \Rightarrow \Delta P_{\theta_i} = \text{sign}(u') * \frac{1}{(\infty - d)} = \frac{1}{\infty} = 0 \quad (10)$$

(no additional correction is required)

In another example, a second test case, e.g., an extreme test case, in which a power of a lens of the tested eye is equal to zero, may be applied to Equation 9. According to this example, the focal length 307 may be equal to infinity, e.g., $P_{eyelens}=0 \Rightarrow f'=\infty$, e.g., as follows:

$$u' = d + L \Rightarrow \Delta P_{\theta_i} = \frac{1}{L'} \quad (11)$$

According to Equation 11, a lens with an effective focal length equal to the length L' between lens 302 and retina 304, e.g., a lens with an EFL=L', may be required.

Referring back to FIG. 1, in some demonstrative embodiments, application 160 may be configured to determine the correction factor, e.g., correction factors 313 and/or 323 (FIG. 3), for example, when a measurement to determine the correction factor is performed via an ophthalmic lens, e.g., as described below.

In some demonstrative embodiments, application 160 may process the depth mapping information from depth information capturing device 118 as depth information captured via an ophthalmic lens, e.g., as described below.

In some demonstrative embodiments, the ophthalmic lens may include a contact lens, an eyeglasses lens, or any other lens.

In some demonstrative embodiments, application 160 may be configured to determine the correction factor, for example, when a patient is wearing spectacles or contact lenses, e.g., including the ophthalmic lens, over the tested eye, for example, during a refraction measurement to determine a correction factor, e.g., as described below.

In some demonstrative embodiments, the effective focal length f' may include an additional power, denoted "$\Delta Pext_{\theta_i}$", which may result from a power of the ophthalmic lens.

Accordingly, the power correction factor $\Delta P_{\theta_i}$ may be constructed from both the effective focal length of the lens of the tested eye and the additional power correction factor $\Delta Pext_{\theta_i}$ of the ophthalmic lens, e.g., as described below.

In some demonstrative embodiments, the additional power $\Delta Pext_{\theta_i}$ may be subtracted from the power correction factor $\Delta P_{\theta_i}$, for example, to determine an adjusted power correction factor, for example, an eye refraction error without the ophthalmic lens, e.g., as described below.

In some demonstrative embodiments, the additional power $\Delta Pext_{\theta_i}$ may be known to the user. For example, the additional power $\Delta Pext_{\theta_i}$ may be noted in a prescription, e.g., including a sphere, a cylinder and/or an axis, of glasses or contact lens of the patient.

In some demonstrative embodiments, application 160 may be configured to determine the adjusted correction factor, for example, with respect to two adjacent sphere-cylindrical lenses, for example, when the patient is wearing the spectacles or the contact lens, e.g., as described below.

In some demonstrative embodiments, the two adjacent sphere-cylindrical lenses may include the lens of the tested eye and an ophthalmic lens.

In one example, the ophthalmic lens may include a contact lens. In another example, the ophthalmic lens may include a lens of eyeglasses.

In some demonstrative embodiments, the power correction factor M may be constructed from both the effective focal length of the lens of the tested eye and the additional power correction factor $\Delta Pext_{\theta_i}$ of the ophthalmic lens, e.g., the contact lens or the lens of the eyeglasses.

In some demonstrative embodiments, application 160 may process the depth mapping information from depth information capturing device 118 as depth information captured via the contact lens on the tested eye, for example, when the user wears the contact lens, e.g., as described below.

In some demonstrative embodiments, application 160 may be configured to determine the adjusted correction factor, for example, when a patient is wearing the contact lens, e.g., as described below.

In some demonstrative embodiments, the additional power $\Delta Pext_{\theta_i}$ may be based on a known power of the ophthalmic lens along a meridian θ, e.g., as follows:

$$\Delta Pext_{\theta_i} = \text{sphere} + \text{cyl}*\sin(\theta - \text{axis})^2 \quad (12)$$

In some demonstrative embodiments, application 160 may be configured to determine the adjusted correction factor, e.g., the tested eye refraction error without the contact lens, for example, by subtracting the additional power $\Delta Pext_{\theta_i}$, e.g., of the ophthalmic lens, for example, as determined by Equation 12, from the power correction factor $\Delta P_{\theta_i}$, e.g., as determined according to Equation 9.

In some demonstrative embodiments, application 160 may be configured to determine the correction factor, for example, when a patient is wearing eyeglasses.

In some demonstrative embodiments, application 160 may process the depth mapping information from depth information capturing device 118 as depth information captured via the lens of eyeglasses at a vertex distance from the tested eye, for example, when the user wears the eyeglasses, e.g., as described below.

In some demonstrative embodiments, application 160 may be configured to determine the power correction factor, for example, based on a vertex distance, denoted "$d_{vert}$", for example, between the tested eye and the lens of the eyeglasses, which may alter the additional power $\Delta Pext_{\theta_i}$, e.g., as follows:

$$\frac{1}{\Delta Pext_{\theta_i}} = \frac{1}{\Delta Pext_{\theta_i}} + d_{vert} \quad (13)$$

In some demonstrative embodiments, the vertex distance $d_{vert}$ may be about 12 mm or any other distance, and it may reduce power of a negative lens and/or may increase a power of a positive lens.

In some demonstrative embodiments, application 160 may be configured to determine the adjusted correction factor, e.g., the tested eye refraction error without the contact lens, for example, by subtracting the additional power $\Delta Pext_{\theta_i}$, e.g., as determined by Equation 13, from the power correction factor $\Delta P_{\theta_i}$ e.g., as determined according to Equation 9.

In some demonstrative embodiments, using an ophthalmic lens, e.g., in eyeglasses or as a contact lens, during the refraction measurement to determine the power correction factor, may assist to overcome one or more inherent limitations of a depth mapper, for example, depth mapper 318, e.g., as described below.

In one example, introducing a positive or a negative ophthalmic lens, e.g., having known power parameters, in front of an eye of a patient may extend a range of a depth measurement. For example, a refractive error of the tested eye may be determined, e.g., in a straightforward manner, based on a refractive error of the entire system and the known power parameters of the ophthalmic lens.

In some demonstrative embodiments, application 160 may be configured to determine the one or more parameters of the refractive error of the tested eye, for example, based on depth mapping information captured by depth information capturing device 118 via a mirror, for example, to increase a distance of a refraction measurement, e.g., as described below.

In some demonstrative embodiments, the depth mapping information may include depth information of an eye of a user captured by depth information capturing device 118 via the mirror, e.g., as described below.

In some demonstrative embodiments, application 160 may be configured to instruct a user to place a camera and/or a sensor, e.g., of depth information capturing device 118, facing a mirror and to capture the depth mapping information on the tested eye via the mirror.

In some demonstrative embodiments, capturing the depth mapping information via the mirror may enable application 160 to analyze the one or more parameters of the refractive error of the tested eye, for example, based on a double optical distance, e.g., to the mirror and back.

In some demonstrative embodiments, application 160 may be configured to determine the one or more parameters of the refractive error of the tested eye, for example, by processing the depth information, e.g., from depth information capturing device 118, as depth information of a ToF depth measurement.

In one example, a ToF depth mapping technique may be based on a time-of-flight principle and/or on a disparity of a point captured at or projected from different coordinates in the real world.

In some demonstrative embodiments, the ToF depth measurement may include a phase shift/time delay, which may be transformed to a distance measurement, for example, under a free space assumption.

In some demonstrative embodiments, the tested eye may be illuminated by a modulated optical signal, and imaged to a sensor plane, for example, using ToF optics.

In some demonstrative embodiments, contributing rays, e.g., except for stray light, for a given pixel may travel about the same optical distance, which may be an imaging condition.

In some demonstrative embodiments, the lens of the tested eye may change an optical distance for the contributing rays, e.g., there will be a different set of rays leaving the tested eye. In case that an illumination path passes through the lens of the tested eye as well, then an overall path difference, e.g., from a lensless scenario, may have two contribution rays, and, as a result, a depth reading may change.

In some demonstrative embodiments, application 160 may be configured to determine a power correction factor of the tested eye, for example, based on the amount of change of the ToF measurement, and one or more configuration parameters of the ToF measurement.

In some demonstrative embodiments, application 160 may be configured to determine a full prescription of a tested eye, for example, including a cylindrical power and an axis of the tested eye, e.g., as described below.

In some demonstrative embodiments, application 160 may be configured to determine a plurality of power correction factors $\theta P_{\theta_i}$ corresponding to a plurality of orientations, for example, to determine the sphere, the cylinder and/or the axis corrections for the tested eye.

In some demonstrative embodiments, application 160 may be configured to determine the plurality of power correction factors $\theta P_{\theta_i}$, for example, while device 102 is rotated, for example, when depth information capturing device 118 includes a one-dimensional depth capturing device configured to produce depth mapping information for a single meridian. For example, the one-dimensional depth mapper may be configured to measure distance to an object along one meridian, e.g., one optical axis of depth information capturing device 118.

In some demonstrative embodiments, application 160 may be configured to instruct a user of device 102 to rotate device 102, for example, according to the plurality of orientations, for example, to capture depth mapping information in the plurality of orientations $\theta_i$.

In some demonstrative embodiments, application 160 may be configured to determine the plurality of power correction factors $\Delta P_{\theta_i}$ for example, based on the depth mapping information in the plurality of orientations $\theta_i$, e.g., according to Equation 9.

In some demonstrative embodiments, the user of device 102 may rotate device 102 along an optical axis of a camera or a sensor of depth information capturing device 118.

In some demonstrative embodiments, the optical axis may be predefined, pre-identified, and/or pre-determined, for example, through a calibration phase.

In some demonstrative embodiments, a plurality of refraction measurements may be performed for the plurality of orientations, for example, when device 102 is rotated around the optical axis of depth information capturing device 118.

In some demonstrative embodiments, the plurality of power correction factors $\theta P_{\theta_i}$ may be determined for some or all of the plurality of orientations $\theta_i$, e.g., a power correction factor $\Delta P_{\theta_i}$, per each orientation $\theta_i$.

In some demonstrative embodiments, an orientation of device 102 may be determined, for example, based on a gyroscope or any other sensor of device 102.

In some demonstrative embodiments, application 160 may be configured to determine a full prescription of the tested eye, for example, based on depth mapping information captured by depth information capturing device 118 while device 102 is rotated, for example, to evaluate a magnification at a meridian.

For example, a user of device 102 may be instructed by application 160 to rotate device 102 between a first relative angle between a depth capturing meridian and a vertical meridian of the tested eye, and a second relative angle, different from the first relative angle, between the depth capturing meridian and the vertical meridian of tested eye.

In some demonstrative embodiments, application 160 may be configured to match the depth information to an ellipse, which may define the sphere, cylinder, and/or an axis of the tested eye.

In one example, two or more different meridians may be suitable, e.g., theoretically, to accurately define the ellipse, for example, to get the full prescription of the cylindrical lens.

Figure 4:
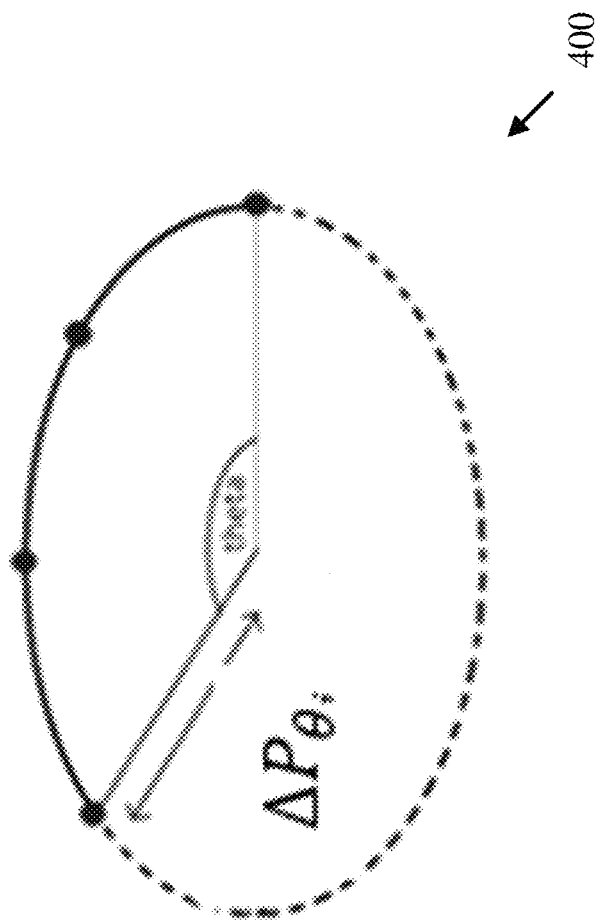
FIG. 4 is a schematic illustration of an ellipse of rotations, in accordance with some demonstrative embodiments.

Reference is made to FIG. 4, which schematically illustrates an ellipse 400 of rotations, in accordance with some demonstrative embodiments.

As shown in FIG. 4, one or more rotations may be suitable to accurately define the ellipse 400, for example, to get a full prescription of a tested eye.

In one example, 5 different rotations, e.g., corresponding to 5 meridians, may be suitable, e.g., theoretically, to accurately define the ellipse, for example, to get the full prescription of the tested lens.

In another example, more than 5 different rotations may be used, for example, to increase an accuracy of the prescription.

In one example, application 160 (FIG. 1) may be configured to instruct a user to change relative rotations between depth information capturing device 118 (FIG. 1) and the tested eye for capturing a plurality of depth mapping information inputs corresponding to a plurality of rotations of ellipse 400.

Referring back to FIG. 1, in some demonstrative embodiments, application 160 may be configured to determine a full prescription of a tested eye, e.g., including a sphere, a cylinder and/or an axis of the tested eye, for example, even without rotation of device 102, e.g., as described below.

In some demonstrative embodiments, depth information capturing device 118 may include a multi-axis depth mapper configured to measure distances across several presets, e.g., meridians. For example, the multi-axis depth mapper may be configured to determine distances across a plurality of depth capturing meridians. For example, the multi-axis depth mapper may determine a first distance across a horizontal axis, e.g., a horizontal depth capturing meridian, a second distance across a vertical axis, e.g., a vertical depth capturing meridian, and a third distance across a 45-degree axis and/or any other axis, e.g., a 45-degree depth capturing meridian.

In some demonstrative embodiments, application 160 may be configured to determine the full prescription of the tested eye, for example, using a single capture of the multi-axis depth mapper. For example, a single capture of the multi-axis depth mapper may be suitable to determine a plurality of power correction factors $\Delta P_{\theta i}$, e.g., a minimal set of power correction factors $\Delta P_{\theta i}$ which may be used to determine the full prescription of the tested eye including the sphere, the cylinder and/or the axis of the tested eye, for example, assuming a slow change of power as a function of a meridian angle.

In some demonstrative embodiments, device 102 may be rotated, for example, along an optical axis of the multi-axis depth mapper, for example, to capture a plurality of depth maps at a plurality of angles, for example, to increase accuracy, and/or to overcome noise during the measurement. For example, a capture may include depths at multiple axes, e.g., at the plurality of depth capturing meridians.

In some demonstrative embodiments, application 160 may be configured to process first and second depth mapping information inputs, the first depth mapping information input corresponds to a first depth capturing meridian of a first depth information capturing device of the multi-axis depth mapper, and the second depth mapping information input corresponds to a second depth capturing meridian of a second depth information capturing device of the multi-axis depth mapper, e.g., as described below.

In some demonstrative embodiments, application 160 may be configured to process the first and second depth mapping information inputs, for example, based on an angle between the first depth capturing meridian of the first depth information capturing device and the second depth capturing meridian of the second depth information capturing device, e.g., as described below.

Figure 5:
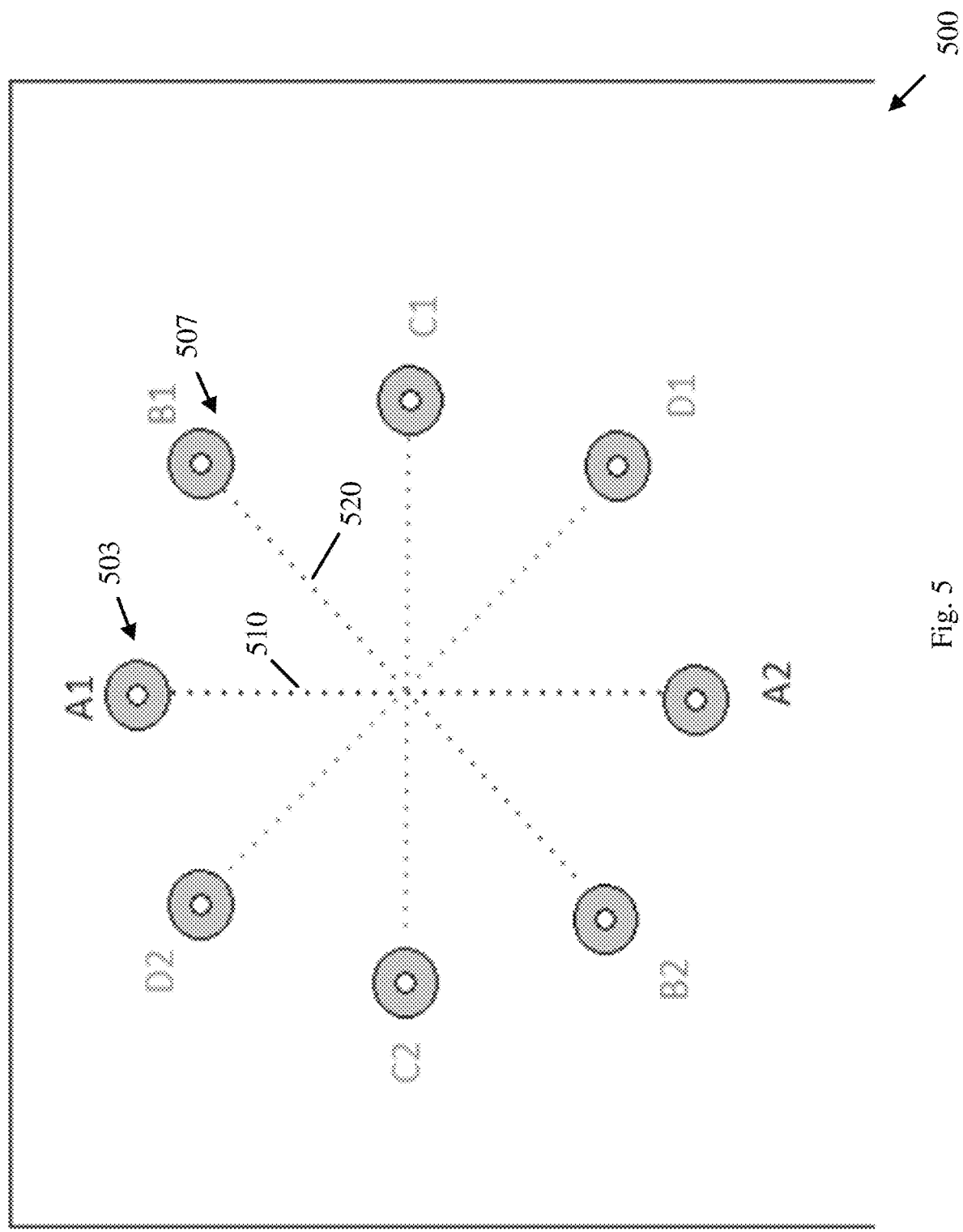
FIG. 5 is a schematic illustration of a multi-axis depth mapper, which may be implemented in accordance with some demonstrative embodiments.

Reference is made to FIG. 5, which schematically illustrates a multi-axis depth mapper 500, which may be implemented in accordance with some demonstrative embodiments.

In some demonstrative embodiments, as shown in FIG. 5, multi-axis depth mapper 500 may include a plurality of depth mappers, e.g., a plurality of one-dimensional depth mappers. For example, a depth mapper of the plurality of depth mappers may include, for example, a stereo or dual camera system, an illuminator and a sensor, or any other configuration of a depth information capturing device.

In some demonstrative embodiments, a depth mapper of the plurality of depth mappers may be configured to provide depth information corresponding to an axis angle of the depth mapper, e.g., a depth capturing meridian of the depth mapper. For example, a first depth mapper 503 including a projector-sensor pair, denoted A1 and A2, may be configured to provide first depth information along a first axis angle 510, e.g., a vertical axis; and/or a second depth mapper 507 including a projector-sensor pair, denoted B1 and B2, may be configured to provide second depth information along a second axis angle 520, e.g., a 45-degree angle.

In some demonstrative embodiments, application 160 (FIG. 1) may be configured to process first depth mapping information input corresponding to the first depth mapper 503, and second depth mapping information input corresponding to the second depth mapper 507.

In some demonstrative embodiments, application 160 (FIG. 1) may be configured to process the first and second depth mapping information inputs for example, based on an angle between first axis angle 510 and second axis angle 520.

Referring back to FIG. 1, in some demonstrative embodiments, depth information capturing device 118 may be configured to provide depth information to determine a power correction factor for a meridian of the tested eye, which corresponds to the axis angle of the depth information capturing device 118.

In some demonstrative embodiments, application 160 may be configured to determine the sensed depth u', for example, based on depth information captured by depth information capturing device 118, e.g., as described below.

In some demonstrative embodiments, application 160 may be configured to use depth information from a depth mapper including an illuminator and a depth sensor, e.g., as described below.

In some demonstrative embodiments, the sensed depth u' may correspond to a depth of a reflex of a feature, e.g., the feature q, on a retina of the tested eye.

In some demonstrative embodiments, the sensed depth u' of the reflex on the retina may be captured, for example, when the reflex from the retina is apparent to a depth sensor of depth information capturing device 118.

In some demonstrative embodiments, application 160 may be configured to instruct a user of device 102 to position depth information capturing device 118, for example, at one or more different distances and/or angles, for example, to enable a depth sensor of depth information capturing device 118 to capture the reflex from the retina.

In some demonstrative embodiments, application 160 may instruct the user to position depth information capturing device 118 relative to the tested eye, for example, according to a method, which may be configured to achieve a uniform reflex from the retina.

Figure 6:
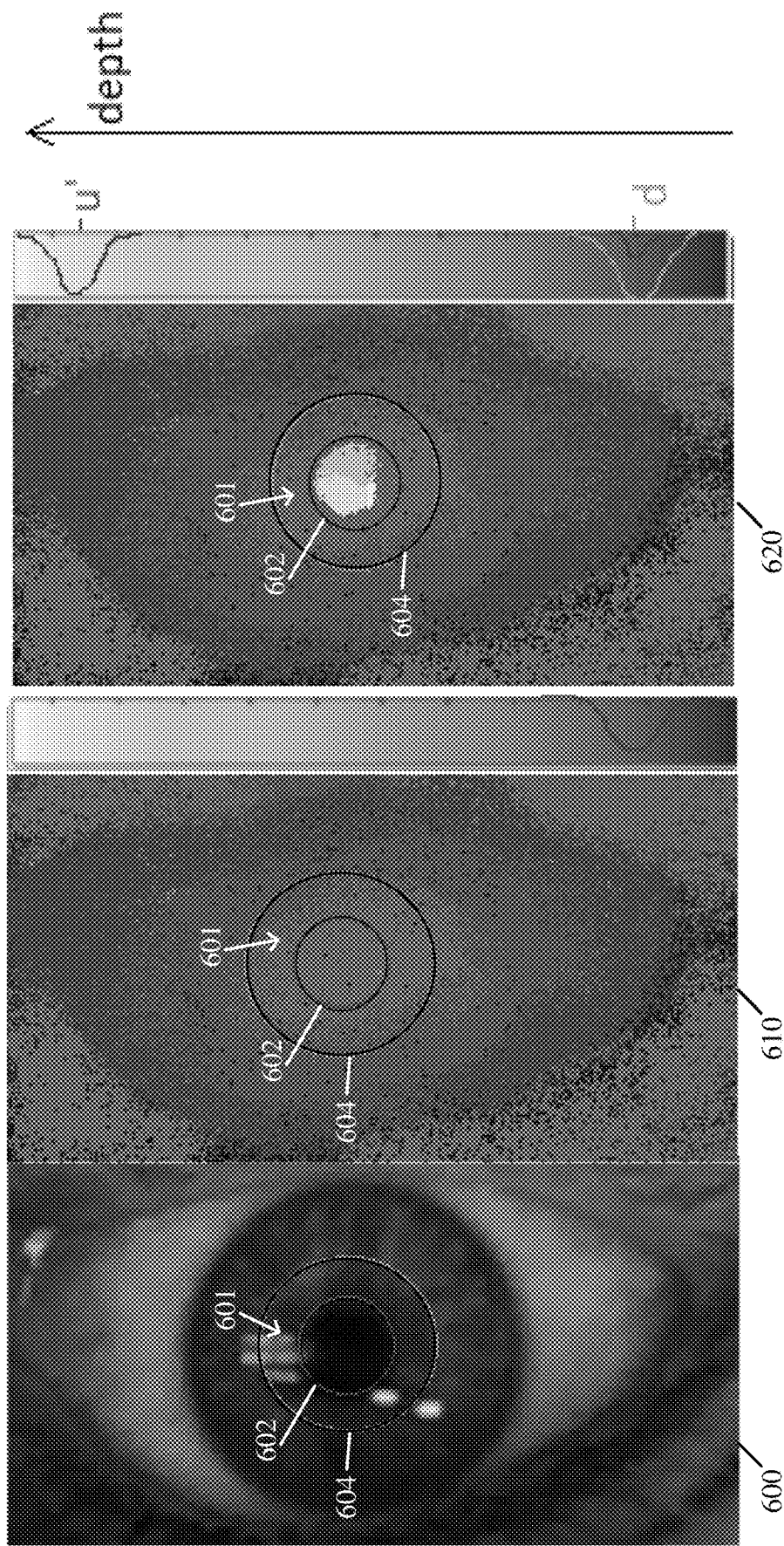
FIG. 6 is a schematic illustration of an image of a tested eye, a first depth map of the tested eye, and a second depth map of the tested eye, in accordance with some demonstrative embodiments.

Reference is made to FIG. 6, which schematically illustrates an image 600 of a tested eye, a first depth map 610 of the tested eye, and a second depth map 620 of the tested eye.

In some demonstrative embodiments, as shown in FIG. 6, a circle 602 may indicate a pupil area of the tested eye, which may be the Region of Interest (ROI) of the tested eye.

In some demonstrative embodiments, as shown in FIG. 6, a circle 604 may indicate an area 601 around the pupil area, e.g., around circle 602.

In some demonstrative embodiments, application 160 (FIG. 1) may be configured to identify a first plurality of depth values corresponding to area 602, to identify a second plurality of depth values corresponding to area 601, and to determine the one or more parameters of the refractive error of the tested eye, for example, based on the first and second pluralities of depth values, e.g., as described below.

In some demonstrative embodiments, application 160 (FIG. 1) may be configured to determine a distance value, for example, based on the first plurality of depth values, to determine a depth value, for example, based on the second plurality of depth values, and to determine the one or more parameters of the refractive error of the tested eye, for example, based on the depth value and the distance value, e.g., as described below.

In some demonstrative embodiments, application 160 (FIG. 1) may be configured to determine whether or not a depth value corresponding to a retina of the tested eye, e.g., a reflex from the retina of the tested eye, is apparent to depth information capturing device 118 (FIG. 1), for example, based on a comparison between depth information in circles 602 and 604, e.g., as described below.

In some demonstrative embodiments, application 160 (FIG. 1) may be configured to determine a distance value, e.g., between depth information capturing device 118 (FIG. 1) and the tested eye, for example, based on depth information in area 601, e.g., as described below.

In some demonstrative embodiments, depth map 610 may include depth information, for example, when the reflex from the retina is not apparent to a depth sensor of depth information capturing device 118 (FIG. 1).

In some demonstrative embodiments, as shown in depth map 610, depth information within circle 602 and in area 601 may be similar.

In some demonstrative embodiments, depth map 620 may include depth information when the reflex from the retina is apparent to the depth sensor of depth information capturing device 118 (FIG. 1).

In some demonstrative embodiments, as shown in depth map 610, depth information within circle 602 may be different from depth information in area 601.

In some demonstrative embodiments, application 160 (FIG. 1) may be configured to determine the depth value, e.g., the depth u', for example, based on a plurality of depth data pixels inside circle 602, e.g., the pupil ROI, in depth map 620, e.g., when the reflex from the retina is apparent to the depth sensor of depth information capturing device 118 (FIG. 1).

In some demonstrative embodiments, application 160 (FIG. 1) may be configured to determine the depth value, e.g., the depth u', for example, based on a mean of a majority of the depth data pixels inside circle 602.

In some demonstrative embodiments, application 160 (FIG. 1) may be configured to determine the distance between depth information capturing device 118 (FIG. 1) and the tested eye, for example, based on a plurality of depth data pixels outside the pupil region of interest, e.g., in area 601.

In some demonstrative embodiments, application 160 (FIG. 1) may be configured to determine the distance between depth information capturing device 118 (FIG. 1) and the tested eye, for example, based on a mean of a majority of the depth data pixels outside the pupil region of interest, e.g., in area 601.

Referring back to FIG. 1, in some demonstrative embodiments, application 160 may be configured to determine depth information of the tested eye, for example, using depth mapping information captured by a depth information capturing device including a plurality of cameras and a light source, e.g., as described below.

In one example, the depth information capturing device 118 may include two cameras. According to this example, a structure of the two cameras may define an axis between the two cameras according to which a distance to an object may be estimated.

In another example, the depth information capturing device 118 may include a plurality of cameras. According to this example, a structure of the plurality of cameras may define a plurality of axes between every pair of cameras, for example, to capture a plurality of depths of an object at once, for example, according to the plurality of axes.

In some demonstrative embodiments, an axis may be related to a certain angle, e.g., meridian of a tested eye, for example, according to the axis of the two cameras.

In some demonstrative embodiments, application 160 may be configured to determine the axis or the plurality of axes of the plurality of cameras, for example, based on settings and/or the deployment of the plurality of cameras.

In some demonstrative embodiments, application 160 may be configured to cause interface 110 to instruct a user to rotate device 102, for example, to capture additional depth readings at additional angles.

In some demonstrative embodiments, application 160 may be configured to determine the depth information, e.g., a distance of a reflex from the retina of the tested eye, based on a light emitted from a light source, which may be in proximity to the cameras, e.g., as described below.

In one example, a flash of device 102 or any other light source, may be suitable to trigger the reflex of the retina.

In some demonstrative embodiments, the distance of the reflex from depth information capturing device 118 may be determined, for example, using a stereo approach from at least two cameras.

In some demonstrative embodiments, application 160 may use one or more methods described above, for example, to increase a dilation of the pupil and/or to increase an accuracy of the refraction measurement, for example, when using depth mapping information from a depth information capturing device 118 including a plurality of cameras and a light source, e.g., as described below.

In some demonstrative embodiments, application 160 may be configured to reduce an error ("accommodation refractive error") which may result from an accommodation state, e.g., as described below.

In some demonstrative embodiments, application 160 may be configured to cause a graphic display of device 102 to display a predefined pattern, for example, configured to reduce an accommodation error of the tested eye, e.g., as described below.

For example, there may be three types, or any other number, of accommodation states, e.g., including a dynamic accommodation state, a tonic accommodation state, and/or a proximal accommodation state.

In some demonstrative embodiments, the tested eye may be drowned to one of the three types of accommodation states, for example, if the correction factor measurement is performed at a finite distance, e.g., between the tested eye and device 102.

In some demonstrative embodiments, application 160 may be configured to cause or trigger a display device, e.g., a display of device 102, to display an image, for example, to reduce and/or inhibit the accommodation refractive error.

In one example, images over a screen of device 102, e.g., a phone screen, may be displayed in way, which may be configured to relax accommodations of the user. For example, one or more predefined images may be displayed to the user in order to exhibit an optical illusion, which may relax an accommodation of the tested eye. For example, the images may be displayed simultaneously during the refraction measurement.

Figure 7:
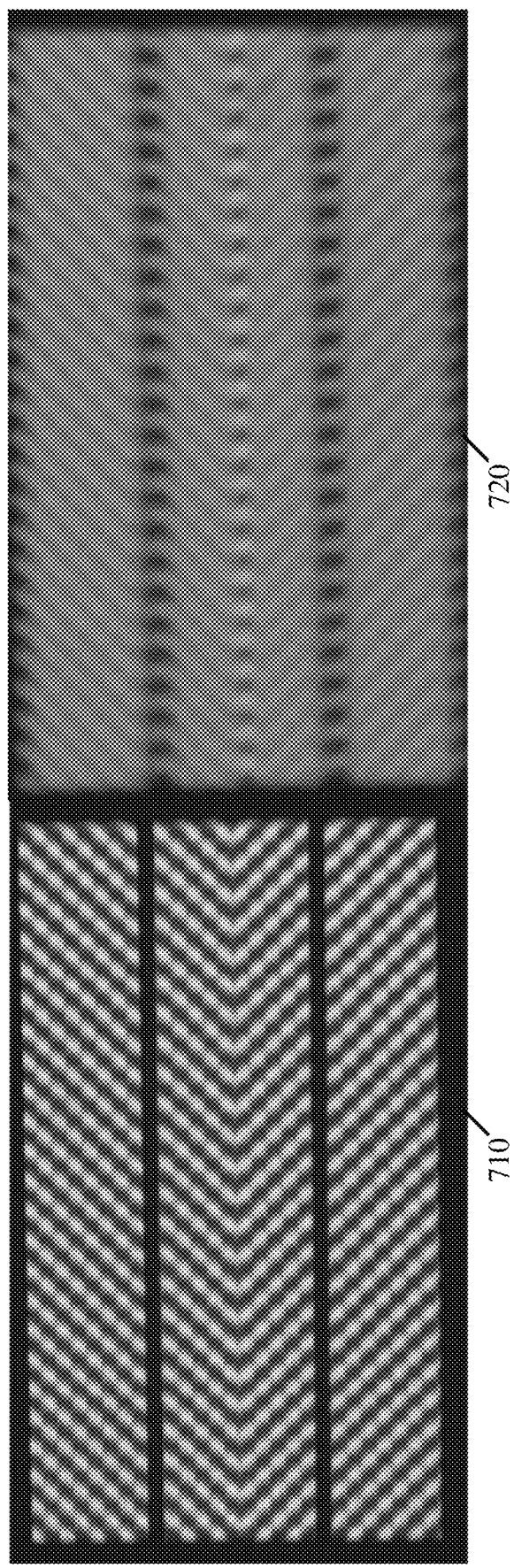
FIG. 7 is a schematic illustration of two images of a pattern, which may be implemented in a measurement, in accordance with some demonstrative embodiments.

Reference is made to FIG. 7, which schematically illustrates two images of a pattern, which may be used in accordance with some demonstrative embodiments.

In some demonstrative embodiments, application 160 (FIG. 1) may be configured to cause a display device, e.g., a display of device 102 (FIG. 1), to display an image 710 including a predefined pattern, for example, which may be configured to reduce and/or inhibit the accommodation refractive error.

In some demonstrative embodiments, the predefined pattern in image 710 may be perceived by a patient as an image 720, for example, when the user is instructed to a stopping point.

Referring back to FIG. 1, in some demonstrative embodiments, application 160 may be configured to combine the refraction measurement with another measurement method, e.g., a subjective measurement method, e.g., as described below.

In some demonstrative embodiments, the subjective measurement method may include displaying images on a display of device 102, and/or analyzing a distance, e.g., an actual distance, between the device 102 and the tested eye of a user.

In some demonstrative embodiments, the refraction measurement may be applied, for example, prior to the subjective measurement, for example, to assess an operation point, e.g., to determine sizes and/or scales of targets, which may fit the patient.

In some demonstrative embodiments, the refraction measurement may be applied, for example, simultaneously with the subjective measurement, for example, to improve accuracy, e.g., of the refraction measurement method.

In some demonstrative embodiments, application 160 may be configured to determine the one or more parameters of the refractive error of the tested, for example, based on depth information captured by depth mapping information capturing device 118, for example, in an environment having poor light conditions, e.g., as described below.

In some demonstrative embodiments, pupils of the tested eye pupil may be naturally dilated and/or an Infrared (IR) light from an IR source of depth information capturing device 118 may not retract a pupil, for example, when the acquisition of the depth mapping information, e.g., by depth information capturing device 118, is in poor light conditions.

In one example, a signal may be received from a larger area in the pupil, which may be utilized to increase an accuracy of a refraction measurement, and/or may ease a user experience, for example, to locate a reflex angle, e.g., when the acquisition of the depth maps is in poor light conditions.

In another example, features in the depth map may be matched solely to the IR light with better signal to noise ratio, for example, from image processing considerations.

Figure 8:
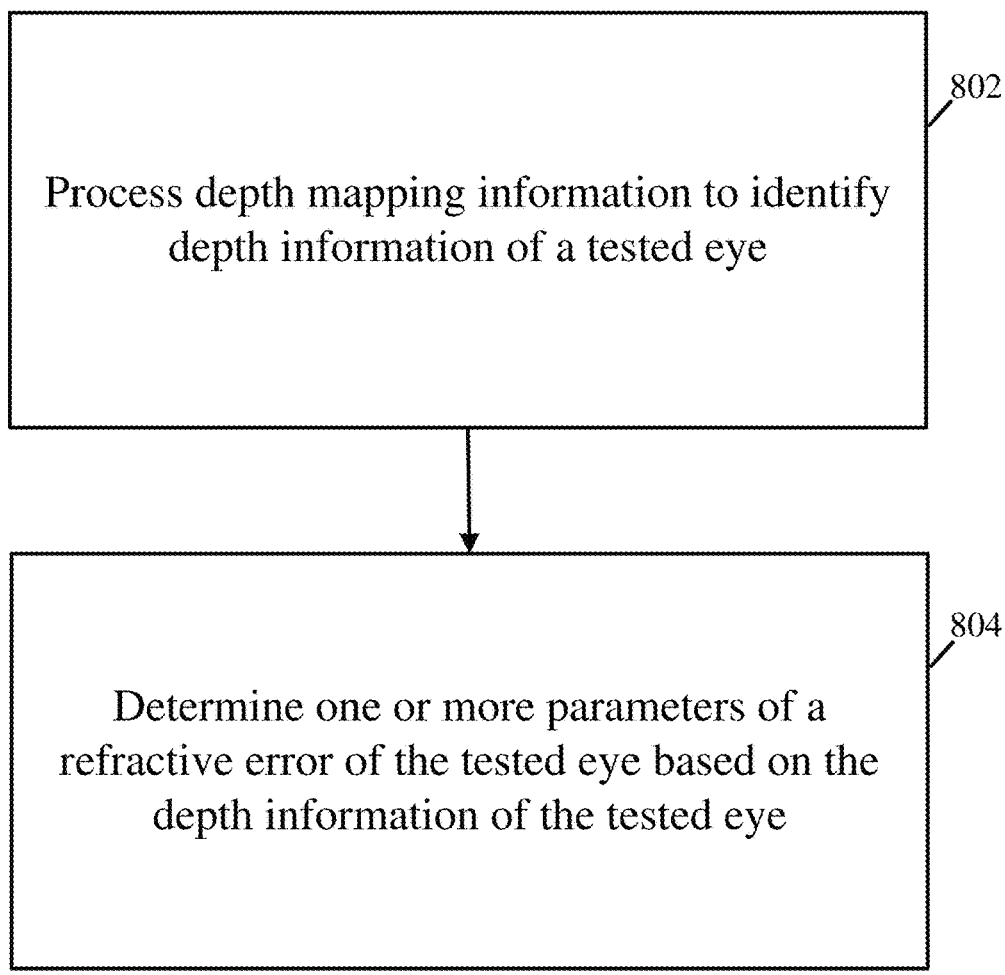
FIG. 8 is a schematic flow-chart illustration of a method of determining one or more parameters of a refractive error of a tested eye, in accordance with some demonstrative embodiments.

Reference is made to FIG. 8, which schematically illustrates a method of determining one or more parameters of a refractive error of a tested eye, in accordance with some demonstrative embodiments. For example, one or more operations of the method of FIG. 14 may be performed by a system, e.g., system 100 (FIG. 1); a device, e.g., device 102 (FIG. 1); a server, e.g., server 170 (FIG. 1); and/or an application, e.g., application 160 (FIG. 1).

In some demonstrative embodiments, as indicated at block 802, the method may include processing depth mapping information to identify depth information of a tested eye. For example, application 160 (FIG. 1) may process the depth mapping information to identify the depth information of the tested eye, e.g., as described above.

In some demonstrative embodiments, as indicated at block 804, the method may include determining one or more parameters of a refractive error of the tested eye based on the depth information of the tested eye. For example, application 160 (FIG. 1) may determine the one or more parameters of the refractive error of the tested eye based on the depth information of the tested eye, e.g., as described above.

Figure 9:
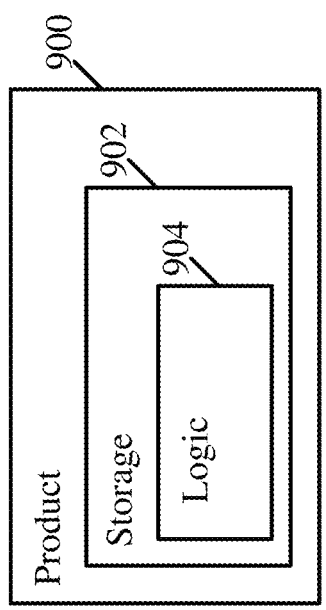
FIG. 9 is a schematic illustration of a product, in accordance with some demonstrative embodiments.

Reference is made to FIG. 9, which schematically illustrates a product of manufacture 900, in accordance with some demonstrative embodiments. Product 900 may include one or more tangible computer-readable ("machine-readable") non-transitory storage media 902, which may include computer-executable instructions, e.g., implemented by logic 904, operable to, when executed by at least one computer processor, enable the at least one computer processor to implement one or more operations at device 102 (FIG. 1), server 170 (FIG. 1), depth information capturing device 118 (FIG. 1), and/or application 160 (FIG. 1), to cause device 102 (FIG. 1), server 170 (FIG. 1), depth information capturing device 118 (FIG. 1), and/or application 160 (FIG. 1) to perform, trigger and/or implement one or more operations and/or functionalities, and/or to perform, trigger and/or implement one or more operations and/or functionalities described with reference to the FIGS. 1, 2, 3, 4, 5, 6, 7 and/or 8, and/or one or more operations described herein. The phrases "non-transitory machine-readable medium" and "computer-readable non-transitory storage media" may be directed to include all computer-readable media, with the sole exception being a transitory propagating signal.

In some demonstrative embodiments, product 900 and/or machine-readable storage medium 902 may include one or more types of computer-readable storage media capable of storing data, including volatile memory, non-volatile memory, removable or non-removable memory, erasable or non-erasable memory, writeable or re-writeable memory, and the like. For example, machine-readable storage medium 902 may include, RAM, DRAM, Double-Data-Rate DRAM (DDR-DRAM), SDRAM, static RAM (SRAM), ROM, programmable ROM (PROM), erasable programmable ROM (EPROM), electrically erasable programmable ROM (EEPROM), Compact Disk ROM (CD-ROM), Compact Disk Recordable (CD-R), Compact Disk Rewriteable (CD-RW), flash memory (e.g., NOR or NAND flash memory), content addressable memory (CAM), polymer memory, phase-change memory, ferroelectric memory, silicon-oxide-nitride-oxide-silicon (SONOS) memory, a disk, a Solid State Drive (SSD), a floppy disk, a hard drive, an optical disk, a magnetic disk, a card, a magnetic card, an optical card, a tape, a cassette, and the like. The computer-readable storage media may include any suitable media involved with downloading or transferring a computer program from a remote computer to a requesting computer carried by data signals embodied in a carrier wave or other propagation medium through a communication link, e.g., a modem, radio or network connection.

In some demonstrative embodiments, logic 904 may include instructions, data, and/or code, which, if executed by a machine, may cause the machine to perform a method, process and/or operations as described herein. The machine may include, for example, any suitable processing platform, computing platform, computing device, processing device, computing system, processing system, computer, processor, or the like, and may be implemented using any suitable combination of hardware, software, firmware, and the like.

In some demonstrative embodiments, logic 904 may include, or may be implemented as, software, a software module, an application, a program, a subroutine, instructions, an instruction set, computing code, words, values, symbols, and the like. The instructions may include any suitable type of code, such as source code, compiled code, interpreted code, executable code, static code, dynamic code, and the like. The instructions may be implemented according to a predefined computer language, manner or syntax, for instructing a processor to perform a certain function. The instructions may be implemented using any suitable high-level, low-level, object-oriented, visual, compiled and/or interpreted programming language, such as C, C++, Java, BASIC, Matlab, Pascal, Visual BASIC, assembly language, machine code, and the like.

Examples

The following examples pertain to further embodiments.

Example 1 includes a product comprising one or more tangible computer-readable non-transitory storage media comprising computer-executable instructions operable to, when executed by at least one computer processor, enable the at least one computer processor to cause a computing device to process depth mapping information to identify depth information of a tested eye; and determine one or more parameters of a refractive error of the tested eye based on the depth information of the tested eye.

Example 2 includes the subject matter of Example 1, and optionally, wherein the instructions, when executed, cause the computing device to identify based on the depth mapping information a depth value captured via a lens of the tested eye, and to determine the one or more parameters of the refractive error of the tested eye based on the depth value.

Example 3 includes the subject matter of Example 2, and optionally, wherein the depth value captured via the lens of the tested eye comprises a depth value corresponding to a retina of the tested eye.

Example 4 includes the subject matter of any one of Examples 1-3, and optionally, wherein the instructions, when executed, cause the computing device to determine the one or more parameters of the refractive error of the tested eye based on a distance between the tested eye and a depth information capturing device by which the depth mapping information is captured.

Example 5 includes the subject matter of Example 4, and optionally, wherein the instructions, when executed, cause the computing device to determine the distance between the tested eye and the depth information capturing device based on the depth mapping information.

Example 6 includes the subject matter of Example 4 or 5, and optionally, wherein the instructions, when executed, cause the computing device to identify based on the depth mapping information a depth value corresponding to a predefined area of the tested eye, and to determine the distance between the tested eye and the depth information capturing device based on the depth value corresponding to the predefined area of the tested eye.

Example 7 includes the subject matter of Example 6, and optionally, wherein the predefined area of the tested eye comprises a sclera of the tested eye or an opaque area around a pupil of the tested eye.

Example 8 includes the subject matter of any one of Examples 4-7, and optionally, wherein the instructions, when executed, cause the computing device to determine the distance between the tested eye and the depth information capturing device based on position information corresponding to a position of the depth information capturing device.

Example 9 includes the subject matter of any one of Examples 4-8, and optionally, wherein the instructions, when executed, cause the computing device to determine the one or more parameters of the refractive error of the tested eye by determining a power correction factor, denoted $\Delta P$, as follows:

$$\Delta P = -\text{sign}(u') * \frac{1}{(u' - d)}$$

wherein u' denotes a depth value based on the depth mapping information, and d denotes a distance value based on the distance between the tested eye and the depth information capturing device.

Example 10 includes the subject matter of any one of Examples 1-9, and optionally, wherein the instructions, when executed, cause the computing device to cause a user interface to instruct a user to position a depth information capturing device facing a mirror such that the depth mapping information is to be captured via the mirror.

Example 11 includes the subject matter of any one of Examples 1-10, and optionally, wherein the instructions, when executed, cause the computing device to identify based on the depth mapping information a first depth value corresponding to a first area of the tested eye, and a second depth value corresponding to a second area of the tested eye, and to determine the one or more parameters of the refractive error of the tested eye based on the first and second depth values.

Example 12 includes the subject matter of Example 11, and optionally, wherein the instructions, when executed, cause the computing device to identify based on the depth mapping information a first plurality of depth values corresponding to the first area of the tested eye, to identify based on the depth mapping information a second plurality of depth values corresponding to the second area of the tested eye, and to determine the one or more parameters of the refractive error of the tested eye based on the first and second pluralities of depth values.

Example 13 includes the subject matter of Example 12, and optionally, wherein the instructions, when executed, cause the computing device to determine a distance value based on the first plurality of depth values, to determine a depth value based on the second plurality of depth values, and to determine the one or more parameters of the refractive error of the tested eye based on the depth value and the distance value.

Example 14 includes the subject matter of any one of Examples 11-13, and optionally, wherein the first area of the tested eye comprises a pupil of the tested eye, and the second area of the tested eye comprises an area around the pupil of the tested eye.

Example 15 includes the subject matter of any one of Examples 1-14, and optionally, wherein the instructions, when executed, cause the computing device to cause a user interface to instruct a user to position a depth information capturing device for capturing the depth mapping information at a predefined distance from the tested eye.

Example 16 includes the subject matter of any one of Examples 1-15, and optionally, wherein the instructions, when executed, cause the computing device to process image information of an image of the tested eye, and to identify the depth information of the tested eye based on the image information.

Example 17 includes the subject matter of any one of Examples 1-16, and optionally, wherein the instructions, when executed, cause the computing device to determine the one or more parameters of the refractive error of the tested eye by processing the depth information as depth information captured via an ophthalmic lens.

Example 18 includes the subject matter of Example 17, and optionally, wherein the instructions, when executed, cause the computing device to determine the one or more parameters of the refractive error of the tested eye by processing the depth information as depth information captured via a lens of eyeglasses at a vertex distance from the tested eye.

Example 19 includes the subject matter of Example 17, and optionally, wherein the instructions, when executed, cause the computing device to determine the one or more parameters of the refractive error of the tested eye by processing the depth information as depth information captured via a contact lens on the tested eye.

Example 20 includes the subject matter of any one of Examples 17-19, and optionally, wherein the instructions, when executed, cause the computing device to determine the one or more parameters of the refractive error of the tested eye based on one or more parameters of the ophthalmic lens.

Example 21 includes the subject matter of any one of Examples 1-20, and optionally, wherein the instructions, when executed, cause the computing device to determine the one or more parameters of the refractive error of the tested eye based on a plurality of different depth mapping information inputs.

Example 22 includes the subject matter of Example 21, and optionally, wherein the plurality of different depth mapping information inputs comprises at least a first depth mapping information input and a second depth mapping information input, the first depth mapping information input captured at a first relative position between a depth information capturing device and the tested eye, the second depth mapping information input captured at a second relative position, different from the first position, between the depth information capturing device and the tested eye.

Example 23 includes the subject matter of Example 22, and optionally, wherein the first relative position comprises a first relative distance between the depth information capturing device and the tested eye, and the second relative position comprises a second relative distance, different from the first relative distance, between the depth information capturing device and the tested eye.

Example 24 includes the subject matter of Example 22 or 23, and optionally, wherein the first relative position comprises a first relative angle between a depth capturing meridian and a vertical meridian of the tested eye, and the second relative position comprises a second relative angle, different from the first relative angle, between the depth capturing meridian and the vertical meridian of tested eye.

Example 25 includes the subject matter of Example 24, and optionally, wherein the instructions, when executed, cause the computing device to process the first and second depth mapping information inputs based on an angle between a first depth capturing meridian of a first depth information capturing device to capture the first depth mapping information input, and a second depth capturing meridian of a second depth information capturing device to capture the second depth mapping information input.

Example 26 includes the subject matter of any one of Examples 22-25, and optionally, wherein the instructions, when executed, cause the computing device to cause a user interface to instruct a user to change a relative positioning between the depth information capturing device and the tested eye for capturing the first depth mapping information input at the first relative position, and the second depth mapping information input at the second relative position.

Example 27 includes the subject matter of any one of Examples 21-26, and optionally, wherein the instructions, when executed, cause the computing device to determine at least one of a cylindrical axis of the tested eye or a cylindrical power of the tested eye based on the plurality of different depth mapping information inputs.

Example 28 includes the subject matter of any one of Examples 1-20, and optionally, wherein the instructions, when executed, cause the computing device to determine the one or more parameters of the refractive error of the tested eye based on depth mapping information comprising a single depth map.

Example 29 includes the subject matter of any one of Examples 1-28, and optionally, wherein the instructions, when executed, cause the computing device to cause a graphic display to display a predefined pattern configured to reduce an accommodation error of the tested eye.

Example 30 includes the subject matter of any one of Examples 1-29, and optionally, wherein the instructions, when executed, cause the computing device to determine the one or more parameters of the refractive error of the tested eye by processing the depth information as depth information of a structured-light depth measurement.

Example 31 includes the subject matter of any one of Examples 1-29, and optionally, wherein the instructions, when executed, cause the computing device to determine the one or more parameters of the refractive error of the tested eye by processing the depth information as depth information of a multi-camera depth measurement.

Example 32 includes the subject matter of any one of Examples 1-29, and optionally, wherein the instructions, when executed, cause the computing device to determine the one or more parameters of the refractive error of the tested eye by processing the depth information as depth information of a Time of Flight (ToF) measurement.

Example 33 includes the subject matter of any one of Examples 1-32, and optionally, wherein the depth mapping information comprises at least one depth map from a depth mapper.

Example 34 includes the subject matter of any one of Examples 1-32, and optionally, wherein the depth mapping information comprises image information from a multi-camera device.

Example 35 includes the subject matter of any one of Examples 1-34, and optionally, wherein the one or more parameters of the refractive error of the tested eye comprise a power correction factor to correct a lens power of the lens of the tested eye.

Example 36 includes the subject matter of any one of Examples 1-35, and optionally, wherein the refractive error comprises at least one of myopia, hyperopia, or astigmatism comprising cylindrical power and cylindrical axis.

Example 37 includes an apparatus comprising a depth information capturing device to generate depth mapping information; and a processor configured to process the depth mapping information to identify depth information of a tested eye, and to determine one or more parameters of a refractive error of the tested eye based on the depth information of the tested eye.

Example 38 includes the subject matter of Example 37, and optionally, wherein the processor is configured to identify based on the depth mapping information a depth value captured via a lens of the tested eye, and to determine the one or more parameters of the refractive error of the tested eye based on the depth value.

Example 39 includes the subject matter of Example 38, and optionally, wherein the depth value captured via the lens of the tested eye comprises a depth value corresponding to a retina of the tested eye.

Example 40 includes the subject matter of any one of Examples 37-39, and optionally, wherein the processor is configured to determine the one or more parameters of the refractive error of the tested eye based on a distance between the tested eye and the depth information capturing device.

Example 41 includes the subject matter of Example 40, and optionally, wherein the processor is configured to determine the distance between the tested eye and the depth information capturing device based on the depth mapping information.

Example 42 includes the subject matter of Example 40 or 41, and optionally, wherein the processor is configured to identify based on the depth mapping information a depth value corresponding to a predefined area of the tested eye, and to determine the distance between the tested eye and the depth information capturing device based on the depth value corresponding to the predefined area of the tested eye.

Example 43 includes the subject matter of Example 42, and optionally, wherein the predefined area of the tested eye comprises a sclera of the tested eye or an opaque area around a pupil of the tested eye.

Example 44 includes the subject matter of any one of Examples 40-43, and optionally, wherein the processor is configured to determine the distance between the tested eye and the depth information capturing device based on position information corresponding to a position of the depth information capturing device.

Example 45 includes the subject matter of any one of Examples 40-44, and optionally, wherein the processor is configured to determine the one or more parameters of the refractive error of the tested eye by determining a power correction factor, denoted $\Delta P$, as follows:

$$\Delta P = -\text{sign}(u') * \frac{1}{(u' - d)}$$

wherein u' denotes a depth value based on the depth mapping information, and d denotes a distance value based on the distance between the tested eye and the depth information capturing device.

Example 46 includes the subject matter of any one of Examples 37-45, and optionally, wherein the processor is configured to cause a user interface to instruct a user to position the depth information capturing device facing a mirror such that the depth mapping information is to be captured via the mirror.

Example 47 includes the subject matter of any one of Examples 37-46, and optionally, wherein the processor is configured to identify based on the depth mapping information a first depth value corresponding to a first area of the tested eye, and a second depth value corresponding to a second area of the tested eye, and to determine the one or more parameters of the refractive error of the tested eye based on the first and second depth values.

Example 48 includes the subject matter of Example 47, and optionally, wherein the processor is configured to identify based on the depth mapping information a first plurality of depth values corresponding to the first area of the tested eye, to identify based on the depth mapping information a second plurality of depth values corresponding to the second area of the tested eye, and to determine the one or more parameters of the refractive error of the tested eye based on the first and second pluralities of depth values.

Example 49 includes the subject matter of Example 48, and optionally, wherein the processor is configured to determine a distance value based on the first plurality of depth values, to determine a depth value based on the second plurality of depth values, and to determine the one or more parameters of the refractive error of the tested eye based on the depth value and the distance value.

Example 50 includes the subject matter of any one of Examples 47-49, and optionally, wherein the first area of the tested eye comprises a pupil of the tested eye, and the second area of the tested eye comprises an area around the pupil of the tested eye.

Example 51 includes the subject matter of any one of Examples 37-50, and optionally, wherein the processor is configured to cause a user interface to instruct a user to position the depth information capturing device for capturing the depth mapping information at a predefined distance from the tested eye.

Example 52 includes the subject matter of any one of Examples 37-51, and optionally, wherein the processor is configured to process image information of an image of the tested eye, and to identify the depth information of the tested eye based on the image information.

Example 53 includes the subject matter of any one of Examples 37-52, and optionally, wherein the processor is configured to determine the one or more parameters of the refractive error of the tested eye by processing the depth information as depth information captured via an ophthalmic lens.

Example 54 includes the subject matter of Example 53, and optionally, wherein the processor is configured to determine the one or more parameters of the refractive error of the tested eye by processing the depth information as depth information captured via a lens of eyeglasses at a vertex distance from the tested eye.

Example 55 includes the subject matter of Example 53, and optionally, wherein the processor is configured to determine the one or more parameters of the refractive error of the tested eye by processing the depth information as depth information captured via a contact lens on the tested eye.

Example 56 includes the subject matter of any one of Examples 53-55, and optionally, wherein the processor is configured to determine the one or more parameters of the refractive error of the tested eye based on one or more parameters of the ophthalmic lens.

Example 57 includes the subject matter of any one of Examples 37-56, and optionally, wherein the processor is configured to determine the one or more parameters of the refractive error of the tested eye based on a plurality of different depth mapping information inputs.

Example 58 includes the subject matter of Example 57, and optionally, wherein the plurality of different depth mapping information inputs comprises at least a first depth mapping information input and a second depth mapping information input, the first depth mapping information input captured at a first relative position between the depth information capturing device and the tested eye, the second depth mapping information input captured at a second relative position, different from the first position, between the depth information capturing device and the tested eye.

Example 59 includes the subject matter of Example 58, and optionally, wherein the first relative position comprises a first relative distance between the depth information capturing device and the tested eye, and the second relative position comprises a second relative distance, different from the first relative distance, between the depth information capturing device and the tested eye.

Example 60 includes the subject matter of Example 58 or 59, and optionally, wherein the first relative position comprises a first relative angle between a depth capturing meridian and a vertical meridian of the tested eye, and the second relative position comprises a second relative angle, different from the first relative angle, between the depth capturing meridian and the vertical meridian of tested eye.

Example 61 includes the subject matter of Example 60, and optionally, wherein the processor is configured to process the first and second depth mapping information inputs based on an angle between a first depth capturing meridian of a first depth information capturing device to capture the first depth mapping information input, and a second depth capturing meridian of a second depth information capturing device to capture the second depth mapping information input.

Example 62 includes the subject matter of any one of Examples 58-61, and optionally, wherein the processor is configured to cause a user interface to instruct a user to change a relative positioning between the depth information capturing device and the tested eye for capturing the first depth mapping information input at the first relative position, and the second depth mapping information input at the second relative position.

Example 63 includes the subject matter of any one of Examples 57-62, and optionally, wherein the processor is configured to determine at least one of a cylindrical axis of the tested eye or a cylindrical power of the tested eye based on the plurality of different depth mapping information inputs.

Example 64 includes the subject matter of any one of Examples 37-56, and optionally, wherein the processor is configured to determine the one or more parameters of the refractive error of the tested eye based on depth mapping information comprising a single depth map.

Example 65 includes the subject matter of any one of Examples 37-64, and optionally, wherein the processor is configured to cause a graphic display to display a predefined pattern configured to reduce an accommodation error of the tested eye.

Example 66 includes the subject matter of any one of Examples 37-65, and optionally, wherein the processor is configured to determine the one or more parameters of the refractive error of the tested eye by processing the depth information as depth information of a structured-light depth measurement.

Example 67 includes the subject matter of any one of Examples 37-65, and optionally, wherein the processor is configured to determine the one or more parameters of the refractive error of the tested eye by processing the depth information as depth information of a multi-camera depth measurement.

Example 68 includes the subject matter of any one of Examples 37-65, and optionally, wherein the processor is configured to determine the one or more parameters of the refractive error of the tested eye by processing the depth information as depth information of a Time of Flight (ToF) measurement.

Example 69 includes the subject matter of any one of Examples 37-68, and optionally, wherein the depth mapping information comprises at least one depth map from a depth mapper.

Example 70 includes the subject matter of any one of Examples 37-68, and optionally, wherein the depth mapping information comprises image information from a multi-camera device.

Example 71 includes the subject matter of any one of Examples 37-70, and optionally, wherein the one or more parameters of the refractive error of the tested eye comprise a power correction factor to correct a lens power of the lens of the tested eye.

Example 72 includes the subject matter of any one of Examples 37-71, and optionally, wherein the refractive error comprises at least one of myopia, hyperopia, or astigmatism comprising cylindrical power and cylindrical axis.

Example 73 includes a method of determining one or more parameters of a refractive error of a tested eye, the method comprising processing depth mapping information to identify depth information of the tested eye; and determining the one or more parameters of the refractive error of the tested eye based on the depth information of the tested eye.

Example 74 includes the subject matter of Example 73, and optionally, comprising identifying based on the depth mapping information a depth value captured via a lens of the tested eye, and determining the one or more parameters of the refractive error of the tested eye based on the depth value.

Example 75 includes the subject matter of Example 74, and optionally, wherein the depth value captured via the lens of the tested eye comprises a depth value corresponding to a retina of the tested eye.

Example 76 includes the subject matter of any one of Examples 73-75, and optionally, comprising determining the one or more parameters of the refractive error of the tested eye based on a distance between the tested eye and a depth information capturing device by which the depth mapping information is captured.

Example 77 includes the subject matter of Example 76, and optionally, comprising determining the distance between the tested eye and the depth information capturing device based on the depth mapping information.

Example 78 includes the subject matter of Example 76 or 77, and optionally, comprising identifying based on the depth mapping information a depth value corresponding to a predefined area of the tested eye, and determining the distance between the tested eye and the depth information capturing device based on the depth value corresponding to the predefined area of the tested eye.

Example 79 includes the subject matter of Example 78, and optionally, wherein the predefined area of the tested eye comprises a sclera of the tested eye or an opaque area around a pupil of the tested eye.

Example 80 includes the subject matter of any one of Examples 76-79, and optionally, comprising determining the distance between the tested eye and the depth information capturing device based on position information corresponding to a position of the depth information capturing device.

Example 81 includes the subject matter of any one of Examples 76-80, and optionally, comprising determining the one or more parameters of the refractive error of the tested eye by determining a power correction factor, denoted ΔP, as follows:

$$\Delta P = -\text{sign}(u') * \frac{1}{(u' - d)}$$

wherein u' denotes a depth value based on the depth mapping information, and d denotes a distance value based on the distance between the tested eye and the depth information capturing device.

Example 82 includes the subject matter of any one of Examples 73-81, and optionally, comprising causing a user interface to instruct a user to position a depth information capturing device facing a mirror such that the depth mapping information is to be captured via the mirror.

Example 83 includes the subject matter of any one of Examples 73-82, and optionally, comprising identifying based on the depth mapping information a first depth value corresponding to a first area of the tested eye, and a second depth value corresponding to a second area of the tested eye, and determining the one or more parameters of the refractive error of the tested eye based on the first and second depth values.

Example 84 includes the subject matter of Example 83, and optionally, comprising identifying based on the depth mapping information a first plurality of depth values corresponding to the first area of the tested eye, identifying based on the depth mapping information a second plurality of depth values corresponding to the second area of the tested eye, and determining the one or more parameters of the refractive error of the tested eye based on the first and second pluralities of depth values.

Example 85 includes the subject matter of Example 84, and optionally, comprising determining a distance value based on the first plurality of depth values, determining a depth value based on the second plurality of depth values, and determining the one or more parameters of the refractive error of the tested eye based on the depth value and the distance value.

Example 86 includes the subject matter of any one of Examples 83-85, and optionally, wherein the first area of the tested eye comprises a pupil of the tested eye, and the second area of the tested eye comprises an area around the pupil of the tested eye.

Example 87 includes the subject matter of any one of Examples 73-86, and optionally, comprising causing a user interface to instruct a user to position a depth information capturing device for capturing the depth mapping information at a predefined distance from the tested eye.

Example 88 includes the subject matter of any one of Examples 73-87, and optionally, comprising processing image information of an image of the tested eye, and identifying the depth information of the tested eye based on the image information.

Example 89 includes the subject matter of any one of Examples 73-88, and optionally, comprising determining the one or more parameters of the refractive error of the tested eye by processing the depth information as depth information captured via an ophthalmic lens.

Example 90 includes the subject matter of Example 89, and optionally, comprising determining the one or more parameters of the refractive error of the tested eye by processing the depth information as depth information captured via a lens of eyeglasses at a vertex distance from the tested eye.

Example 91 includes the subject matter of Example 89, and optionally, comprising determining the one or more parameters of the refractive error of the tested eye by processing the depth information as depth information captured via a contact lens on the tested eye.

Example 92 includes the subject matter of any one of Examples 89-91, and optionally, comprising determining the one or more parameters of the refractive error of the tested eye based on one or more parameters of the ophthalmic lens.

Example 93 includes the subject matter of any one of Examples 73-92, and optionally, comprising determining the one or more parameters of the refractive error of the tested eye based on a plurality of different depth mapping information inputs.

Example 94 includes the subject matter of Example 93, and optionally, wherein the plurality of different depth mapping information inputs comprises at least a first depth mapping information input and a second depth mapping information input, the first depth mapping information input captured at a first relative position between a depth information capturing device and the tested eye, the second depth mapping information input captured at a second relative position, different from the first position, between the depth information capturing device and the tested eye.

Example 95 includes the subject matter of Example 94, and optionally, wherein the first relative position comprises a first relative distance between the depth information capturing device and the tested eye, and the second relative position comprises a second relative distance, different from the first relative distance, between the depth information capturing device and the tested eye.

Example 96 includes the subject matter of Example 94 or 95, and optionally, wherein the first relative position comprises a first relative angle between a depth capturing meridian and a vertical meridian of the tested eye, and the second relative position comprises a second relative angle, different from the first relative angle, between the depth capturing meridian and the vertical meridian of tested eye.

Example 97 includes the subject matter of Example 96, and optionally, comprising processing the first and second depth mapping information inputs based on an angle between a first depth capturing meridian of a first depth information capturing device to capture the first depth mapping information input, and a second depth capturing meridian of a second depth information capturing device to capture the second depth mapping information input.

Example 98 includes the subject matter of any one of Examples 94-97, and optionally, comprising causing a user interface to instruct a user to change a relative positioning between the depth information capturing device and the tested eye for capturing the first depth mapping information input at the first relative position, and the second depth mapping information input at the second relative position.

Example 99 includes the subject matter of any one of Examples 93-98, and optionally, comprising determining at least one of a cylindrical axis of the tested eye or a cylindrical power of the tested eye based on the plurality of different depth mapping information inputs.

Example 100 includes the subject matter of any one of Examples 73-92, and optionally, comprising determining the one or more parameters of the refractive error of the tested eye based on depth mapping information comprising a single depth map.

Example 101 includes the subject matter of any one of Examples 73-100, and optionally, comprising causing a graphic display to display a predefined pattern configured to reduce an accommodation error of the tested eye.

Example 102 includes the subject matter of any one of Examples 73-101, and optionally, comprising determining the one or more parameters of the refractive error of the tested eye by processing the depth information as depth information of a structured-light depth measurement.

Example 103 includes the subject matter of any one of Examples 73-101, and optionally, comprising determining the one or more parameters of the refractive error of the tested eye by processing the depth information as depth information of a multi-camera depth measurement.

Example 104 includes the subject matter of any one of Examples 73-101, and optionally, comprising determining the one or more parameters of the refractive error of the tested eye by processing the depth information as depth information of a Time of Flight (ToF) measurement.

Example 105 includes the subject matter of any one of Examples 73-104, and optionally, wherein the depth mapping information comprises at least one depth map from a depth mapper.

Example 106 includes the subject matter of any one of Examples 73-104, and optionally, wherein the depth mapping information comprises image information from a multi-camera device.

Example 107 includes the subject matter of any one of Examples 73-106, and optionally, wherein the one or more parameters of the refractive error of the tested eye comprise a power correction factor to correct a lens power of the lens of the tested eye.

Example 108 includes the subject matter of any one of Examples 73-107, and optionally, wherein the refractive error comprises at least one of myopia, hyperopia, or astigmatism comprising cylindrical power and cylindrical axis.

Example 109 includes an apparatus of determining one or more parameters of a refractive error of a tested eye, the apparatus comprising means for processing depth mapping information to identify depth information of the tested eye; and means for determining the one or more parameters of the refractive error of the tested eye based on the depth information of the tested eye.

Example 110 includes the subject matter of Example 109, and optionally, comprising means for identifying based on the depth mapping information a depth value captured via a lens of the tested eye, and determining the one or more parameters of the refractive error of the tested eye based on the depth value.

Example 111 includes the subject matter of Example 110, and optionally, wherein the depth value captured via the lens of the tested eye comprises a depth value corresponding to a retina of the tested eye.

Example 112 includes the subject matter of any one of Examples 109-111, and optionally, comprising means for determining the one or more parameters of the refractive error of the tested eye based on a distance between the tested eye and a depth information capturing device by which the depth mapping information is captured.

Example 113 includes the subject matter of Example 112, and optionally, comprising means for determining the distance between the tested eye and the depth information capturing device based on the depth mapping information.

Example 114 includes the subject matter of Example 112 or 113, and optionally, comprising means for identifying based on the depth mapping information a depth value corresponding to a predefined area of the tested eye, and determining the distance between the tested eye and the depth information capturing device based on the depth value corresponding to the predefined area of the tested eye.

Example 115 includes the subject matter of Example 114, and optionally, wherein the predefined area of the tested eye comprises a sclera of the tested eye or an opaque area around a pupil of the tested eye.

Example 116 includes the subject matter of any one of Examples 112-115, and optionally, comprising means for determining the distance between the tested eye and the depth information capturing device based on position information corresponding to a position of the depth information capturing device.

Example 117 includes the subject matter of any one of Examples 112-116, and optionally, comprising means for determining the one or more parameters of the refractive error of the tested eye by determining a power correction factor, denoted ΔP, as follows:

$$\Delta P = -\text{sign}(u') * \frac{1}{(u' - d)}$$

wherein u' denotes a depth value based on the depth mapping information, and d denotes a distance value based on the distance between the tested eye and the depth information capturing device.

Example 118 includes the subject matter of any one of Examples 109-117, and optionally, comprising means for causing a user interface to instruct a user to position a depth information capturing device facing a mirror such that the depth mapping information is to be captured via the mirror.

Example 119 includes the subject matter of any one of Examples 109-118, and optionally, comprising means for identifying based on the depth mapping information a first depth value corresponding to a first area of the tested eye, and a second depth value corresponding to a second area of the tested eye, and determining the one or more parameters of the refractive error of the tested eye based on the first and second depth values.

Example 120 includes the subject matter of Example 119, and optionally, comprising means for identifying based on the depth mapping information a first plurality of depth values corresponding to the first area of the tested eye, identifying based on the depth mapping information a second plurality of depth values corresponding to the second area of the tested eye, and determining the one or more parameters of the refractive error of the tested eye based on the first and second pluralities of depth values.

Example 121 includes the subject matter of Example 120, and optionally, comprising means for determining a distance value based on the first plurality of depth values, determining a depth value based on the second plurality of depth values, and determining the one or more parameters of the refractive error of the tested eye based on the depth value and the distance value.

Example 122 includes the subject matter of any one of Examples 119-121, and optionally, wherein the first area of the tested eye comprises a pupil of the tested eye, and the second area of the tested eye comprises an area around the pupil of the tested eye.

Example 123 includes the subject matter of any one of Examples 109-122, and optionally, comprising means for causing a user interface to instruct a user to position a depth information capturing device for capturing the depth mapping information at a predefined distance from the tested eye.

Example 124 includes the subject matter of any one of Examples 109-123, and optionally, comprising means for processing image information of an image of the tested eye, and identifying the depth information of the tested eye based on the image information.

Example 125 includes the subject matter of any one of Examples 109-124, and optionally, comprising means for determining the one or more parameters of the refractive error of the tested eye by processing the depth information as depth information captured via an ophthalmic lens.

Example 126 includes the subject matter of Example 125, and optionally, comprising means for determining the one or more parameters of the refractive error of the tested eye by processing the depth information as depth information captured via a lens of eyeglasses at a vertex distance from the tested eye.

Example 127 includes the subject matter of Example 125, and optionally, comprising means for determining the one or more parameters of the refractive error of the tested eye by processing the depth information as depth information captured via a contact lens on the tested eye.

Example 128 includes the subject matter of any one of Examples 125-127, and optionally, comprising means for determining the one or more parameters of the refractive error of the tested eye based on one or more parameters of the ophthalmic lens.

Example 129 includes the subject matter of any one of Examples 109-128, and optionally, comprising means for determining the one or more parameters of the refractive error of the tested eye based on a plurality of different depth mapping information inputs.

Example 130 includes the subject matter of Example 129, and optionally, wherein the plurality of different depth mapping information inputs comprises at least a first depth mapping information input and a second depth mapping information input, the first depth mapping information input captured at a first relative position between a depth information capturing device and the tested eye, the second depth mapping information input captured at a second relative position, different from the first position, between the depth information capturing device and the tested eye.

Example 131 includes the subject matter of Example 130, and optionally, wherein the first relative position comprises a first relative distance between the depth information capturing device and the tested eye, and the second relative position comprises a second relative distance, different from the first relative distance, between the depth information capturing device and the tested eye.

Example 132 includes the subject matter of Example 130 or 131, and optionally, wherein the first relative position comprises a first relative angle between a depth capturing meridian and a vertical meridian of the tested eye, and the second relative position comprises a second relative angle, different from the first relative angle, between the depth capturing meridian and the vertical meridian of tested eye.

Example 133 includes the subject matter of Example 132, and optionally, comprising means for processing the first and second depth mapping information inputs based on an angle between a first depth capturing meridian of a first depth information capturing device to capture the first depth mapping information input, and a second depth capturing meridian of a second depth information capturing device to capture the second depth mapping information input.

Example 134 includes the subject matter of any one of Examples 130-133, and optionally, comprising means for causing a user interface to instruct a user to change a relative positioning between the depth information capturing device and the tested eye for capturing the first depth mapping information input at the first relative position, and the second depth mapping information input at the second relative position.

Example 135 includes the subject matter of any one of Examples 129-134, and optionally, comprising means for determining at least one of a cylindrical axis of the tested eye or a cylindrical power of the tested eye based on the plurality of different depth mapping information inputs.

Example 136 includes the subject matter of any one of Examples 109-128, and optionally, comprising means for determining the one or more parameters of the refractive error of the tested eye based on depth mapping information comprising means for a single depth map.

Example 137 includes the subject matter of any one of Examples 109-136, and optionally, comprising means for causing a graphic display to display a predefined pattern configured to reduce an accommodation error of the tested eye.

Example 138 includes the subject matter of any one of Examples 109-137, and optionally, comprising means for determining the one or more parameters of the refractive error of the tested eye by processing the depth information as depth information of a structured-light depth measurement.

Example 139 includes the subject matter of any one of Examples 109-137, and optionally, comprising means for determining the one or more parameters of the refractive error of the tested eye by processing the depth information as depth information of a multi-camera depth measurement.

Example 140 includes the subject matter of any one of Examples 109-137, and optionally, comprising means for determining the one or more parameters of the refractive error of the tested eye by processing the depth information as depth information of a Time of Flight (ToF) measurement.

Example 141 includes the subject matter of any one of Examples 109-140, and optionally, wherein the depth mapping information comprises at least one depth map from a depth mapper.

Example 142 includes the subject matter of any one of Examples 109-140, and optionally, wherein the depth mapping information comprises image information from a multi-camera device.

Example 143 includes the subject matter of any one of Examples 109-142, and optionally, wherein the one or more parameters of the refractive error of the tested eye comprise a power correction factor to correct a lens power of the lens of the tested eye.

Example 144 includes the subject matter of any one of Examples 109-143, and optionally, wherein the refractive error comprises at least one of myopia, hyperopia, or astigmatism comprising means for cylindrical power and cylindrical axis.

Functions, operations, components and/or features described herein with reference to one or more embodiments, may be combined with, or may be utilized in combination with, one or more other functions, operations, components and/or features described herein with reference to one or more other embodiments, or vice versa.

While certain features have been illustrated and described herein, many modifications, substitutions, changes, and equivalents may occur to those skilled in the art. It is, therefore, to be understood that the appended claims are intended to cover all such modifications and changes as fall within the true spirit of the disclosure.

What is claimed is:

1. A product comprising one or more tangible computer-readable non-transitory storage media comprising computer-executable instructions operable to, when executed by at least one computer processor, enable the at least one computer processor to cause a computing device to:
process depth mapping information to identify depth information of a tested eye, the depth information including a plurality of different depth mapping information inputs; and
determine one or more parameters of a refractive error of the tested eye based on the plurality of different depth mapping information inputs of the depth information of the tested eye.

2. The product of claim 1, wherein the instructions, when executed, cause the computing device to identify based on the depth mapping information a depth value captured via a lens of the tested eye, and to determine the one or more parameters of the refractive error of the tested eye based on the depth value.

3. The product of claim 1, wherein the instructions, when executed, cause the computing device to determine the one or more parameters of the refractive error of the tested eye based on a distance between the tested eye and a depth information capturing device by which the depth mapping information is captured.

4. The product of claim 3, wherein the instructions, when executed, cause the computing device to determine the distance between the tested eye and the depth information capturing device based on the depth mapping information.

5. The product of claim 3, wherein the instructions, when executed, cause the computing device to identify based on the depth mapping information a depth value corresponding to a predefined area of the tested eye, and to determine the distance between the tested eye and the depth information capturing device based on the depth value corresponding to the predefined area of the tested eye.

6. The product of claim 5, wherein the predefined area of the tested eye comprises a sclera of the tested eye or an opaque area around a pupil of the tested eye.

7. The product of claim 3, wherein the instructions, when executed, cause the computing device to determine the one or more parameters of the refractive error of the tested eye by determining a power correction factor, denoted ΔP, as follows:

$$\Delta P = -\text{sign}(u') * \frac{1}{(u'-d)}$$

wherein u' denotes a depth value based on the depth mapping information, and d denotes a distance value based on the distance between the tested eye and the depth information capturing device.

8. The product of claim 1, wherein the instructions, when executed, cause the computing device to identify based on the depth mapping information a first depth value corresponding to a first area of the tested eye, and a second depth value corresponding to a second area of the tested eye, and to determine the one or more parameters of the refractive error of the tested eye based on the first and second depth values.

9. The product of claim 8, wherein the instructions, when executed, cause the computing device to identify based on the depth mapping information a first plurality of depth values corresponding to the first area of the tested eye, to identify based on the depth mapping information a second plurality of depth values corresponding to the second area of the tested eye, and to determine the one or more parameters of the refractive error of the tested eye based on the first and second pluralities of depth values.

10. The product of claim 9, wherein the instructions, when executed, cause the computing device to determine a distance value based on the first plurality of depth values, to determine a depth value based on the second plurality of depth values, and to determine the one or more parameters of the refractive error of the tested eye based on the depth value and the distance value.

11. The product of claim 8, wherein the first area of the tested eye comprises a pupil of the tested eye, and the second area of the tested eye comprises an area around the pupil of the tested eye.

12. The product of claim 1, wherein the instructions, when executed, cause the computing device to cause a user interface to instruct a user to position a depth information capturing device for capturing the depth mapping information at a predefined distance from the tested eye.

13. The product of claim 1, wherein the instructions, when executed, cause the computing device to process image information of an image of the tested eye, and to identify the depth information of the tested eye based on the image information.

14. The product of claim 1, wherein the instructions, when executed, cause the computing device to determine the one or more parameters of the refractive error of the tested eye by processing the depth information as depth information captured via an ophthalmic lens.

15. The product of claim 14, wherein the instructions, when executed, cause the computing device to determine the one or more parameters of the refractive error of the tested eye based on one or more parameters of the ophthalmic lens.

16. The product of claim 1, wherein the plurality of different depth mapping information inputs comprises at least a first depth mapping information input and a second depth mapping information input, the first depth mapping information input captured at a first relative position between a depth information capturing device and the tested eye, the second depth mapping information input captured at a second relative position, different from the first relative position, between the depth information capturing device and the tested eye.

17. The product of claim 16, wherein the first relative position comprises a first relative distance between the depth information capturing device and the tested eye, and the second relative position comprises a second relative distance, different from the first relative distance, between the depth information capturing device and the tested eye.

18. The product of claim 16, wherein the first relative position comprises a first relative angle between a depth capturing meridian of the tested eye and a vertical meridian of the tested eye, and the second relative position comprises a second relative angle, different from the first angle, between the depth capturing meridian and the vertical meridian of the tested eye.

19. The product of claim 16, wherein the instructions, when executed, cause the computing device to cause a user interface to instruct a user to change a relative positioning between the depth information capturing device and the tested eye for capturing the first depth mapping information input at the first relative position, and the second depth mapping information input at the second relative position.

20. The product of claim 1, wherein the instructions, when executed, cause the computing device to determine at least one of a cylindrical axis of the tested eye or a cylindrical power of the tested eye based on the plurality of different depth mapping information inputs.

21. The product of claim 1, wherein the instructions, when executed, cause the computing device to determine the one or more parameters of the refractive error of the tested eye based on depth mapping information comprising a single depth map.

22. The product of claim 1, wherein the instructions, when executed, cause the computing device to determine the one or more parameters of the refractive error of the tested eye by processing the depth information as depth information of a structured-light depth measurement.

23. The product of claim 1, wherein the instructions, when executed, cause the computing device to determine the one or more parameters of the refractive error of the tested eye by processing the depth information as depth information of a Time of Flight (ToF) measurement.

24. The product of claim 1, wherein the depth mapping information comprises at least one depth map from a depth mapper.

25. The product of claim 1, wherein the depth mapping information comprises image information from a multi-camera device.

26. The product of claim 1, wherein the one or more parameters of the refractive error of the tested eye comprise a power correction factor to correct a lens power of a lens of the tested eye.

27. The product of claim 1, wherein the refractive error comprises at least one of myopia, hyperopia, or astigmatism comprising cylindrical power and cylindrical axis.

28. An apparatus comprising:
a depth information capturing device to generate depth mapping information; and
a processor configured to process the depth mapping information to identify depth information of a tested eye including a plurality of different depth mapping information inputs, and the processor being configured to determine one or more parameters of a refractive error of the tested eye based on the plurality of different depth mapping information inputs of the depth information of the tested eye.

29. The apparatus of claim 28, wherein the processor is configured to determine the one or more parameters of the refractive error of the tested eye based on a distance between the tested eye and the depth information capturing device.

30. A product comprising one or more tangible computer-readable non-transitory storage media comprising computer-executable instructions operable to, when executed by at least one computer processor, enable the at least one computer processor to cause a computing device to:

process depth mapping information of a tested eye to identify a first depth value corresponding to a first area of the tested eye and a second depth value corresponding to a second area of the tested eye; and determine the one or more parameters of the refractive error of the tested eye based on the first and second depth values of the depth mapping information of the tested eye.

31. The product of claim 30, wherein the instructions, when executed, cause the computing device to determine the one or more parameters of the refractive error of the tested eye based on a distance between the tested eye and a depth information capturing device by which the depth mapping information is captured.

32. The product of claim 30, wherein the instructions, when executed, cause the computing device to cause a user interface to instruct a user to position a depth information capturing device for capturing the depth mapping information at a predefined distance from the tested eye.

33. The product of claim 30, wherein the instructions, when executed, cause the computing device to process image information of an image of the tested eye, and to identify the depth mapping information of the tested eye based on the image information.

34. The product of claim 30, wherein the instructions, when executed, cause the computing device to determine the one or more parameters of the refractive error of the tested eye by processing the depth mapping information as depth information captured via an ophthalmic lens.

35. The product of claim 30, wherein the instructions, when executed, cause the computing device to determine the one or more parameters of the refractive error of the tested eye based on depth mapping information comprising a single depth map.

36. The product of claim 30, wherein the instructions, when executed, cause the computing device to determine the one or more parameters of the refractive error of the tested eye by processing the depth mapping information as depth information of a structured-light depth measurement.

37. The product of claim 30, wherein the instructions, when executed, cause the computing device to determine the one or more parameters of the refractive error of the tested eye by processing the depth mapping information as depth information of a Time of Flight (ToF) measurement.

38. The product of claim 30, wherein the depth mapping information comprises image information from a multi-camera device.

* * * * *